US011186624B2

(12) United States Patent
Bertoletti et al.

(10) Patent No.: US 11,186,624 B2
(45) Date of Patent: Nov. 30, 2021

(54) HBV ANTIGEN SPECIFIC BINDING MOLECULES AND FRAGMENTS THEREOF

(71) Applicant: Lion TCR Pte. Ltd., Singapore (SG)

(72) Inventors: Antonio Bertoletti, Singapore (SG); Tan Anthony Tanoto, Singapore (SG); Sheau Fung Sarene Koh, Singapore (SG); Zack Ho, Singapore (SG)

(73) Assignee: Lion TCR Pte. Ltd.

( * ) Notice: Subject to any disclaimer, the term of this patent is extended or adjusted under 35 U.S.C. 154(b) by 430 days.

(21) Appl. No.: 16/336,000

(22) PCT Filed: Sep. 23, 2016

(86) PCT No.: PCT/SG2016/050469
§ 371 (c)(1),
(2) Date: Mar. 22, 2019

(87) PCT Pub. No.: WO2018/056897
PCT Pub. Date: Mar. 29, 2018

(65) Prior Publication Data
US 2019/0233497 A1  Aug. 1, 2019

(51) Int. Cl.
| | | |
|---|---|---|
| *C07K 14/725* | (2006.01) |
| *C12Q 1/70* | (2006.01) |
| *C07K 14/005* | (2006.01) |
| *A61P 35/00* | (2006.01) |
| *A61P 31/00* | (2006.01) |
| *A61P 31/20* | (2006.01) |
| *C12Q 1/6883* | (2018.01) |
| *G01N 33/576* | (2006.01) |
| *C12Q 1/6886* | (2018.01) |
| *G01N 33/569* | (2006.01) |
| *A61K 35/17* | (2015.01) |
| *C12Q 1/6881* | (2018.01) |
| *A61K 38/00* | (2006.01) |

(52) U.S. Cl.
CPC .......... *C07K 14/7051* (2013.01); *A61K 35/17* (2013.01); *A61P 31/00* (2018.01); *A61P 31/20* (2018.01); *A61P 35/00* (2018.01); *C07K 14/005* (2013.01); *C12Q 1/6881* (2013.01); *C12Q 1/6883* (2013.01); *C12Q 1/6886* (2013.01); *C12Q 1/706* (2013.01); *G01N 33/56972* (2013.01); *G01N 33/5761* (2013.01); *A61K 38/00* (2013.01); *C12N 2730/10122* (2013.01); *C12N 2740/10043* (2013.01); *C12N 2800/22* (2013.01); *C12Q 2600/106* (2013.01); *G01N 2333/7051* (2013.01)

(58) Field of Classification Search
CPC ................................................ C07K 14/7051
See application file for complete search history.

(56) References Cited

U.S. PATENT DOCUMENTS

| 2011/0070208 A1 | 3/2011 | Bertoletti et al. |
| 2012/0308580 A1 | 12/2012 | Bertoletti et al. |

FOREIGN PATENT DOCUMENTS

| WO | 2009136874 A1 | 11/2009 |
| WO | 2011062562 A1 | 5/2011 |

OTHER PUBLICATIONS

International Search Report PCT/SG2016/050469, dated Jan. 16, 2017.
Rooney, Cliona M., et al., "Infusion of Cytotoxic T Cells for the Prevention and Treatment of Epstein-Barr Virus-Induced Lymphoma in Allogeneic Transplant Recipients." Blood, vol. 92, No. 5 Sep. 1, 1998; pp. 1549-1555.
Maus et al., "Adoptive Immunotherapy for Cancer or Viruses" Annu Rev Immunol, 2014; 32:189-225, doi: 10.1146/aunnurev-immunol 132713-120136.
Zaritskay et al., "New Flow Cytometric Assays For MOnitoring Cell-Mediated Cytotoxicity." Expert Rev Vaccinese Jun. 2010; 9(6): pp. 601-616. doi 10.1586/erv.10.49.
T. Jake Liang, "Hepatitis B: The Visur and Disease." Hepatology, May 2009; 49(5 Suppl): S13-S21, doi 10.1002/hep.22881.
Cobbold et al., "Adoptive Transfer of Cytomegalovirus-Specific CTL to Stem Cell Transplant Patients After Selection by HLA-Peptide Tetramers." vol. 202, No. 3, Aug. 1, 2005 pp. 379-386.
Qasim et al., "Immunotherapy of HCC metastases with autologous T cell receptor redirected T cells, targeting HBsAg in a liver transplant patient."Journal of Hepatology 2015 vol. 62, pp. 486-491.
Koh et al., "A Practical Approach to Immunotherapy of Hepatocellular Carcinoma Using T Cells Redirected Against Hepatitis B Virus." MOlecular Therapy-Nucleic Acids (2013) vol. 2, e114.
Tanet al., "Building and Optimizing a Virus-specific T Cell Receptor Library for Targeted Immunotherapy in Viral Infections" Feb. 25, 2014 88 (2) pp. 1332-1341.

*Primary Examiner* — Scott Long
(74) *Attorney, Agent, or Firm* — Lerner, David, Littenberg, Krumholz & Mentlik, LLP

(57) ABSTRACT

Hepatitis B Virus (HBV) antigen specific binding molecules, in particular T Cell Receptors (TCRs), TCR polypeptides and fragments thereof. The invention is also related to modified cells containing the TCRs, TCR polypeptides or fragments, pharmaceutical composition or kits including the same or methods of making or using the same as is described. In particular, the invention discloses TCRs or a fragments thereof, capable of binding to a peptide of a Hepatitis B Virus (HBV) Env polypeptide presented by an MHC class I molecule comprising an MHC class I σ-chain encoded by an HLA-Cw*08 allele.

21 Claims, 20 Drawing Sheets

Specification includes a Sequence Listing.

unstimulated
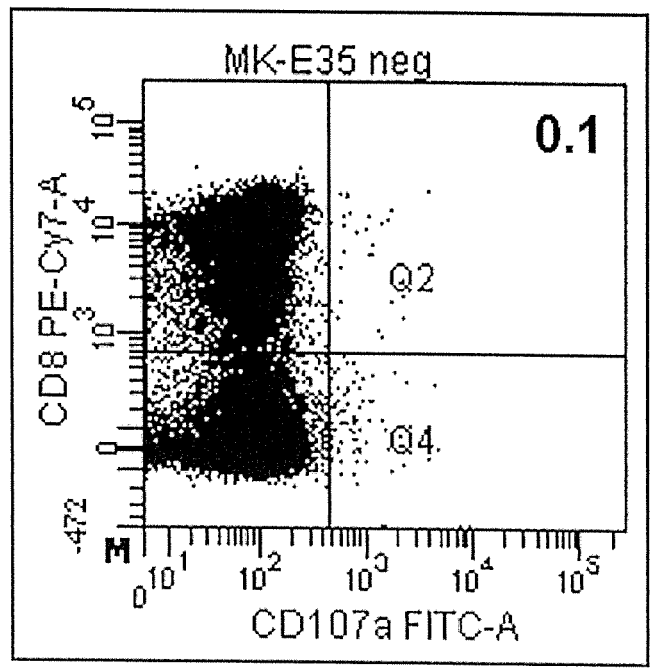
+ E35 peptide
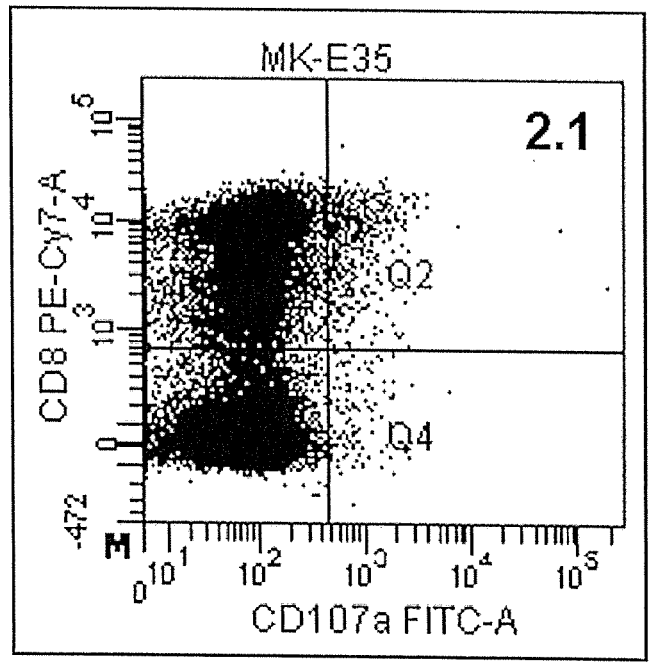
Figure 3

| AA no. | Name | Amino Acid Sequence | |
|---|---|---|---|
| 166-180 | 15 mer HBVC Env 34 | STTSGFLGPLLVLQA | |
| 171-185 | 15 mer HBVC Env 35 | FLGPLLVLQAGFFLL | |
| 170-179 | Env 34-1 | GLLGPLLVLQ | ⎫ |
| 170-180 | Env 34-2 | GLLGPLLVLQA | |
| 171-180 | Env 34-3 | LLGPLLVLQA | |
| 172-180 | Env 34-4 | LGPLLVLQA | ⎬ Gen B |
| 171-181 | Env 34-5 | LLGPLLVLQAG | |
| 172-181 | Env 34-6 | LGPLLVLQAG | |
| 173-181 | Env 34-7 | GPLLVLQAG | ⎭ |
| 170-180 | Env 34-8 | GFLGPLLVLQA | ⎫ |
| 171-180 | Env 34-9 | FLGPLLVLQA | ⎬ Gen C/D |
| 171-181 | Env 34-10 | FLGPLLVLQAG | ⎭ |

Figure 6A

Alpha chain

| | | |
|---|---|---|
| CDR1a: | DXSSTY | (SEQ ID NO: 1), or |
| | DSSSTY | (SEQ ID NO:24), or |
| | DISSTY | (SEQ ID NO:25) |
| CDR2a: | IFSNMDM | (SEQ ID NO: 2) |
| CDR3a: | AETLDNYGQNFV | (SEQ ID NO: 3) |

Where X = S or I

Beta chain

| | | |
|---|---|---|
| CDR1b: | DFQATT | (SEQ ID NO: 4) |
| CDR2b: | SNEGSKA | (SEQ ID NO: 5) |
| CDR3b: | SAVDRDEPFHSNQPQH | (SEQ ID NO: 6) |

| | Before Codon Optimization | After Codon Optimization |
|---|---|---|
| CDR1a (where CDR1a = DSSSTY (SEQ ID NO: 24) | gacagctcctccacctac (SEQ ID NO: 7) | gactcctctagtacctac (SEQ ID NO: 13) |
| CDR2a | attttttcaaatatggacatg (SEQ ID NO: 8) | atcttttccaacatggacatg (SEQ ID NO: 14) |
| CDR3a | gcagagaccttggataactatggtcagaattttgtc (SEQ ID NO: 9) | gccgagaccctggacaactacggccagaatttcgtg (SEQ ID NO: 15) |
| CDR1b | gactttcaggccacaact (SEQ ID NO: 10) | gacttccaggccaccaca (SEQ ID NO: 16) |
| CDR2b | tccaatgagggctccaaggcc (SEQ ID NO: 11) | agcaacgaaggatccaaagcc (SEQ ID NO: 17) |
| CDR3b | agtgctgtagacagggatgaacctttccatagcaatcagccccagcat (SEQ ID NO: 12) | tcagcagtggaccgagatgaacctttccacagcaaccagccacagcat (SEQ ID NO: 18) |

Figure 11

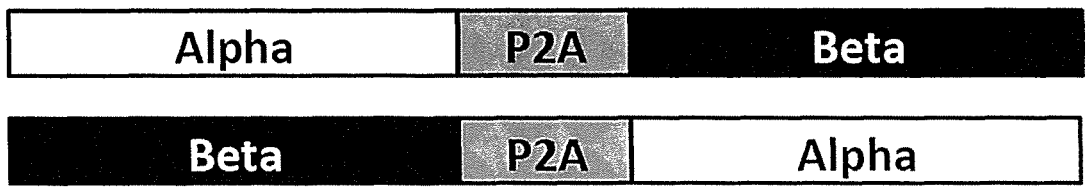
Figure 16
Vb Staining
MOCK 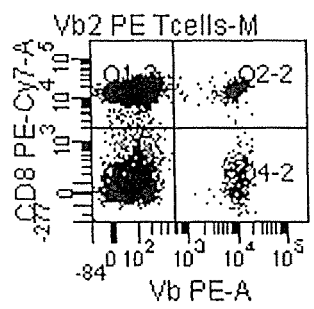
Vα-P2A-Vβ 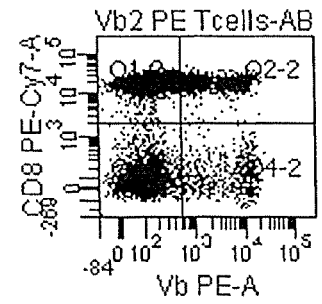
Vβ-P2A-Vα 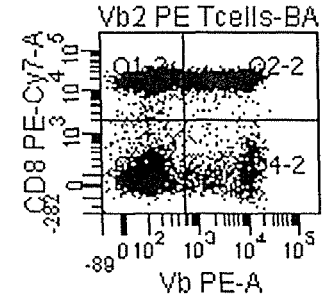
Figure 17

Pentamer Staining
MOCK
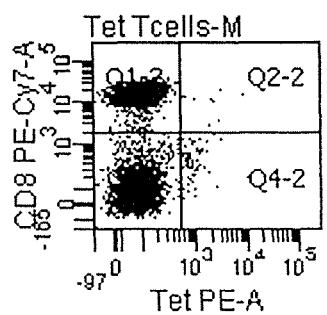
| Population | #Events | %Parent |
|---|---|---|
| Q1-2 | 6,420 | 70.0 |
| Q2-2 | 12 | 0.1 |
| Q3-2 | 2,655 | 29.0 |
| Q4-2 | 81 | 0.9 |
Specimen Name: Tet Tcells
Tube Name: M
Vα-P2A-Vβ
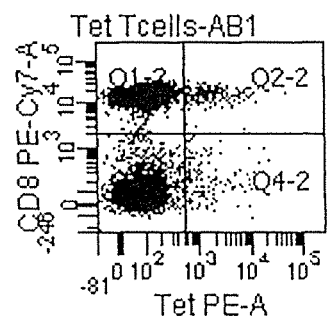
Specimen Name: Tet Tcells
Tube Name: AB1
| Population | #Events | %Parent |
|---|---|---|
| Q1-2 | 6,864 | 68.4 |
| Q2-2 | 215 | 2.1 |
| Q3-2 | 2,810 | 28.0 |
| Q4-2 | 151 | 1.5 |
Vβ-P2A-Vα
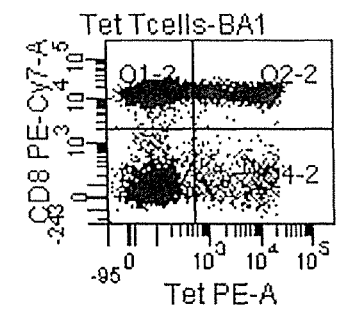
Specimen Name: Tet Tcells
Tube Name: BA1
| Population | #Events | %Parent |
|---|---|---|
| Q1-2 | 5,521 | 55.0 |
| Q2-2 | 1,405 | 14.0 |
| Q3-2 | 2,524 | 25.1 |
| Q4-2 | 592 | 5.9 |
Figure 17 (cont.)

HBV ANTIGEN SPECIFIC BINDING MOLECULES AND FRAGMENTS THEREOF

CROSS-REFERENCE TO RELATED APPLICATIONS

The present application is a national phase entry under 35 U.S.C. § 371 of International Application No. PCT/SG2016/050469 filed Sep. 23, 2016, published as International Publication No. WO 2018/056897 A1, incorporated herein by reference.

FIELD OF THE INVENTION

The present invention relates to an Hepatitis B Virus (HBV) antigen specific-binding molecules, in particular T Cell Receptors (TCRs), TCR polypeptides and fragments thereof.

BACKGROUND OF THE INVENTION

The host immune system act through T cells to combat viral infection and keep host cancerous growth in check. In hepatitis B virus infection particularly, CD8+ T cells are an important component of the immune system to clear or control viral infections. Patients that resolve the infection has quantitatively stronger CD8+ immune responses compare to chronically infected patients. Whereas lack of a virus-specific T cell response is associated with failure to control chronic HBV infection. Reconstitution of virus-specific immunity, either through bone marrow transplant or adoptive transfer of virus-specific T cells can control persistent infection, and protect against lethal infection.

External pathogen, such as virus, can be processed into short peptides and presented by HLA class I molecules on the surface of an antigen presenting cell (APC). T cell receptor (TCR) expressed on CD8+ T cells can associate with peptide presented by a specific HLA class I molecules on APC. Thereafter, a TCR act by recognising the HLA-peptide complex and initiating series of cellular changes to lyse infected cells. Strategies to manipulate the T cell response via virus-specific TCR could lead to clinical therapies to treat chronic infections or prevent mortality related to further complications caused by prolonged infections. In particular, Hepatocellular carcinoma (HCC) cells often have HBV DNA integration and can be targeted by HBV-specific T cells.

The HLA class I molecules encoded by major histocompatibility complex (MHC) class I exhibit polymorphism, where different allelic forms of HLA-A, B or C can be found in different individuals. Conventionally, effort of identifying HBV specific epitopes has been bias towards HLA-A2 molecule against HBV genotypes A, D, and F, which is dominant in western population. In contrast, there was every limited information regarding HLA-B or C-restricted epitopes against HBV genotypes B and C, which is dominant in Asian population.

In this particular application, we have constructed a TCR sequence against a HBV envelope protein 171-180 restricted by a prominent Asian allele HLA-Cw*08.

SUMMARY OF THE INVENTION

The present invention is concerned with antigen-binding molecules, in particular T Cell Receptors (TCRs). More specifically the present invention is concerned with antigen-binding molecules and cells capable of recognising a peptide of Hepatitis B Virus.

In one aspect, the present invention provides a TCR, or a fragment thereof, optionally isolated, comprising:
  a TCR α-chain variable region comprising a CDR3a having the amino acid sequence:

```
CDR3a:
                                       (SEQ ID NO: 3)
         AETLDNYGQNFV,
``` or a variant thereof in which one or two amino acids are replaced with another amino acid; and;
  a TCR β-chain variable region comprising a CDR3b having the amino acid sequence:

```
CDR3b:
                                       (SEQ ID NO: 6)
         SAVDRDEPFHSNQPQH
``` or a variant thereof in which one or two amino acids are replaced with another amino acid.

In some embodiments, the TCR or a fragment comprises:
  a TCR α-chain variable region comprising CDRs having the amino acid sequences i) to iii):

```
i)
                                       (SEQ ID NO: 1)
         CDR1a: DXSSTY;

ii)
                                       (SEQ ID NO: 2)
         CDR2a: IFSNMDM;

iii)
                                       (SEQ ID NO: 3)
         CDR3a: AETLDNYGQNFV;
``` and;
  a TCR β-chain variable region comprising CDRs having the amino acid sequences iv) to vi):

```
iv)
                                       (SEQ ID NO: 4)
         CDR1b: DFQATT;

v)
                                       (SEQ ID NO: 5)
         CDR2b: SNEGSKA;

vi)
                                       (SEQ ID NO: 6)
         CDR3b: SAVDRDEPFHSNQPQH;
``` or a variant thereof in which one or two amino acids in one or more of the sequences i) to vi) are replaced with another amino acid
  where X=S or I.

In another aspect, the present invention provides a TCR, or a fragment thereof, optionally isolated, comprising:
  a TCR α-chain variable region comprising CDRs having the amino acid sequences i) to iii):

```
i)
                                       (SEQ ID NO: 1)
         CDR1a: DXSSTY;
```

```
        ii)
                                         (SEQ ID NO: 2)
        CDR2a: IFSNMDM;

iii)
                                         (SEQ ID NO: 3)
        CDR3a: AETLDNYGQNFV;
``` or a variant thereof in which one or two amino acids in one or more of the sequences i) to iii) are replaced with another amino acid;

where X=S or I.

In another aspect, the present invention provides a TCR, or a fragment thereof, optionally isolated, comprising:

a TCR β-chain variable region comprising CDRs having the amino acid sequences iv) to vi):

```
        iv)
                                         (SEQ ID NO: 4)
        CDR1b: DFQATT;

v)
                                         (SEQ ID NO: 5)
        CDR2b: SNEGSKA;

vi)
                                         (SEQ ID NO: 6)
        CDR3b: SAVDRDEPFHSNQPQH;
``` or a variant thereof in which one or two amino acids in one or more of the sequences iv) to vi) are replaced with another amino acid.

In embodiments in accordance with various aspects of the present invention the TCR or a fragment is capable of binding to a peptide of a Hepatitis B Virus (HBV) Env polypeptide presented by an MHC class I molecule comprising an MHC class I α-chain encoded by an HLA-Cw*08 allele.

In one aspect the present invention provides a TCR or a fragment thereof, optionally isolated, comprising an α-chain variable region and a β-chain variable region, wherein the TCR or fragment is capable of binding to a peptide of a HBV Env polypeptide presented by an MHC class I molecule comprising an MHC class I α-chain encoded by an HLA-Cw*08 allele.

In embodiments in accordance with various aspects of the present invention the peptide of a HBV Env polypeptide comprises positions 171-180 of HBV Env polypeptide. In some embodiments, the peptide comprises or consists of the amino acid sequence FLGPLLVLQA (SEQ ID NO: 19) or LLGPLLVLQA (SEQ ID NO: 20).

In embodiments in accordance with various aspects of the present invention the HLA-Cw*08 allele is HLA-Cw*0801. In some embodiments, the HLA-Cw*08 allele is not HLA-Cw*0801.

In another aspect, the present invention provides an isolated nucleic acid encoding a TCR or fragment according to the present invention. In some embodiments, the isolated nucleic acid comprises:

(a) a nucleic acid sequence encoding a TCR α-chain comprising a variable region and a constant region;

(b) a nucleic acid sequence encoding a TCR β-chain comprising a variable region and a constant region; and (c) a nucleic acid sequence encoding a cleavable linker;

wherein sequence (c) is located in the isolated nucleic acid between sequences (a) and (b), and wherein sequences (a), (b) and (c) are in the same reading frame. In some embodiments, the sequences (a), (b) and (c) are provided with the 5' to 3' orientation: 5'-(b)-(c)-(a)-3'. In some embodiments the cleavable linker is a Picornavirus 2A (P2A) linker. In some embodiments the constant region of the TCR α-chain and/or the constant region of the TCR β-chain additionally encode at least one non-native cysteine residue for forming a disulphide bond between the TCR α-chain and TCRβ-chain.

In another aspect the present invention provides a vector comprising an isolated nucleic acid according to the present invention, wherein the vector is selected from a group consists of plasmids, binary vectors, DNA vectors, mRNA vectors, retrovial vectors, lentivial vectors, transposon-based vectors, and artificial chromosomes.

In another aspect, the present invention provides an isolated polypeptide encoded by an isolated nucleic acid or vector according to the present invention.

In another aspect, the present invention provides an isolated TCR α-chain variable region polypeptide, comprising CDRs having the amino acid sequences i) to iii):

```
        i)
                                         (SEQ ID NO: 1)
        CDR1a: DXSSTY;

ii)
                                         (SEQ ID NO: 2)
        CDR2a: IFSNMDM;

iii)
                                         (SEQ ID NO: 3)
        CDR3a: AETLDNYGQNFV;
``` or a variant thereof in which one or two amino acids in one or more of the sequences i) to iii) are replaced with another amino acid;

where X=S or I.

In some embodiments, the isolated TCR α-chain variable region polypeptide, comprises CDRs having the amino acid sequences i) to iii):

```
        i)
                                         (SEQ ID NO: 24)
        CDR1a: DSSSTY;

ii)
                                         (SEQ ID NO: 2)
        CDR2a: IFSNMDM;

iii)
                                         (SEQ ID NO: 3)
        CDR3a: AETLDNYGQNFV;
``` or a variant thereof in which one or two amino acids in one or more of the sequences i) to iii) are replaced with another amino acid.

In some embodiments, the isolated TCR α-chain variable region polypeptide, comprises CDRs having the amino acid sequences i) to iii):

```
        i)
                                         (SEQ ID NO: 25)
        CDR1a: DISSTY;

ii)
                                         (SEQ ID NO: 2)
        CDR2a: IFSNMDM;

iii)
                                         (SEQ ID NO: 3)
        CDR3a: AETLDNYGQNFV;
``` or a variant thereof in which one or two amino acids in one or more of the sequences i) to iii) are replaced with another amino acid.

In another aspect, the present invention provides an isolated TCR β-chain variable region polypeptide comprising CDRs having the amino acid sequences iv) to vi):

iv)
(SEQ ID NO: 4)
CDR1b: DFQATT;

v)
(SEQ ID NO: 5)
CDR2b: SNEGSKA;

vi)
(SEQ ID NO: 6)
CDR3b: SAVDRDEPFHSNQPQH;

or a variant thereof in which one or two amino acids in one or more of the sequences iv) to vi) are replaced with another amino acid.

In another aspect, the present invention provides a cell, optionally isolated, comprising a TCR or fragment, an isolated nucleic acid, a vector or an isolated polypeptide according to the present invention.

In another aspect, the present invention provides a cell, optionally isolated, comprising an exogenous TCR reactive to a peptide of a HBV Env polypeptide presented by an MHC class I molecule comprising an MHC class I α-chain encoded by an HLA-Cw*08 allele.

In embodiments in accordance with aspects of the present invention a cell displays one or more of the following properties:
a) expression of IFNγ;
b) cytotoxicity to a cell infected with HBV or comprising or expressing an HBV Env peptide or polypeptide;
c) proliferation, increased IFNγ expression, increased IL-2 expression, increased TNFα expression, increased perforin expression, increased granzyme expression and/or increased FAS ligand (FASL) expression in response to contact with a cell infected with HBV or comprising or expressing an HBV Env peptide or polypeptide;

In another aspect, the present invention provides an in vitro method of producing a HBV reactive T cell, comprising introducing into a cell an isolated nucleic acid or vector according to the present invention. In some embodiments, the method of additionally comprises culturing the cell under conditions suitable for expression of the isolated nucleic acid or vector by the cell.

In a related aspect, the present invention provides a cell, optionally isolated, which is obtained or obtainable by the method of producing a HBV reactive T cell according to the present invention.

In another aspect, the present invention provides a complex, optionally an in vitro complex, comprising a TCR, fragment, polypeptide, or cell according to the present invention and a HBV Env peptide or polypeptide, optionally further comprising an MHC class I molecule comprising an MHC class I α-chain encoded by an HLA-Cw*08 allele.

In another aspect, the present invention provides a pharmaceutical composition comprising a TCR, fragment, isolated nucleic acid, vector, isolated polypeptide or cell according to the present invention and a pharmaceutically acceptable carrier, adjuvant, excipient, or diluent.

In another aspect, the present invention provides the use of a TCR or fragment, an isolated nucleic acid, a vector, an isolated polypeptide, cell or pharmaceutical composition according to the present invention in the manufacture of a medicament for treating or preventing a disease or disorder.

In another aspect, the present invention provides a method of treating or preventing a disease or disorder, comprising administering to a subject a therapeutically or prophylactically effective amount of a TCR or fragment, an isolated nucleic acid, a vector, an isolated polypeptide, cell or pharmaceutical composition according to the present invention.

In another aspect, the present invention provides a method of treating or preventing a disease or disorder in a subject, comprising:
(a) isolating at least one T cell from a subject;
(b) introducing into the at least one T cell an isolated nucleic acid or vector according to the present invention, thereby modifying the at least one T cell; and
(c) administering the modified at least one T cell to the subject.

In one aspect, the present invention provides a method of treating or preventing a disease or disorder in a subject, comprising:
(a) isolating at least one T cell from a subject;
(b) modifying the at least one T cell to express or comprise a TCR, fragment, nucleic acid, vector, or polypeptide according to the present invention, and;
(c) administering the modified at least one T cell to a subject.

In some embodiments, the subject from which the T cell is isolated is the subject administered with the modified T cell.

In embodiments in accordance with various aspects of the present invention the disease or disorder is caused or exacerbated by HBV infection, or is a disease or disorder for which HBV infection is a risk factor. In some embodiments, the disease is one or more of hepatitis B, hepatocellular carcinoma or pancreatic cancer. In some embodiments, the subject to be treated has an HLA-C genotype comprising an HLA-Cw*08 allele. In some embodiments, the HLA-Cw*08 allele is HLA-Cw*0801. In some embodiments the HLA-Cw*08 allele is not HLA-Cw*0801. In some embodiments, the subject is infected with, or is at risk of infection by, HBV. In some embodiments, the HBV is selected from HBV genotype A, B, C, D, E, F, G, H, I or J.

In one aspect, the present invention provides an in vitro method for preparing a modified T cell, the method comprising introducing into a T cell a TCR or fragment, an isolated nucleic acid, a vector, or an isolated polypeptide according to the present invention. In particular embodiments, the method comprises introducing an isolated nucleic acid or vector according to the invention. In some embodiments, introducing an isolated nucleic acid or vector according to the invention comprises transduction. In some embodiments, introducing a nucleic acid or vector according to the invention comprises electroporation.

In another aspect the present invention provides a method of identifying a subject for therapeutic or prophylactic treatment of a disease or disorder using a TCR or fragment, an isolated nucleic acid, a vector, an isolated polypeptide, a cell or a pharmaceutical composition according to the present invention, the method comprising determining the HLA-C genotype for the subject, wherein a subject determined to have an HLA-Cw*08 allele is identified as being a subject suitable for therapeutic or prophylactic treatment. In some embodiments, the HLA-Cw*08 allele is HLA-Cw*0801. In some embodiments, the HLA-Cw*08 allele is not HLA-Cw*0801.

In another aspect the present invention provides a method of identifying a subject for therapeutic or prophylactic treatment of a disease or disorder using a TCR or fragment, an isolated nucleic acid, a vector, an isolated polypeptide, a cell or pharmaceutical composition according to the present invention, the method comprising determining whether the subject is infected with, or determining whether the subject is at risk of infection by, HBV. In some embodiments the HBV is selected from HBV genotype A, B, C, D, E, F, G, H, I or J.

In another aspect, the present invention provides a method for diagnosing HBV infection in a subject, the method comprising detecting in a sample obtained from a subject, optionally in vitro the presence of a TCR or fragment, a complex, an isolated nucleic acid, a vector, an isolated polypeptide or a cell according to the present invention. In some embodiments, the HBV is selected from HBV genotype A, B, C, D, E, F, G, H, I or J. In some embodiments, the subject has an HLA-Cw*08 allele. In some embodiments, the HLA-Cw*08 allele is HLA-Cw*0801. In some embodiments, the HLA-Cw*08 allele is not HLA-Cw*0801.

In another aspect, the present invention provides a kit of parts comprising a predetermined quantity of a TCR or fragment, an isolated nucleic acid, a vector, an isolated polypeptide, a cell or a pharmaceutical composition according to the present invention.

Description

T Cell Receptor

T Cell Receptors (TCRs) are heterodimeric, antigen-binding molecules typically comprising an α-chain and a β-chains. In nature, α-chain and β-chains are expressed at the cell surface of T cells (αβ T cells) as a complex with invariant CD3 chains. An alternative TCR comprising γ and δ chains is expressed on a subset of T cells (γδ T cells). TCRs recognise (bind to) antigen peptide presented by major histocompatibility complex (MHC) molecules. TCR structure and recognition of the peptide-MHC complex is described in detail for example in Immunobiology, 5th Edn. Janeway C A Jr, Travers P, Walport M, et al. New York: Garland Science (2001), Chapters 3 and 6, which are hereby incorporated by reference in their entirety.

TCR α-chain and β-chains comprise a constant (C) region, and a variable (V) region. The variable regions of the α-chain and β-chain polypeptides bind to the antigen-MHC complex. Each TCR α-chain and β-chain variable region comprises three complementary determining regions (CDRs), which determine specificity for the antigen-MHC complex. The CDRs for the TCR α-chain and β-chain are respectively designated CDR1-3a and CDR1-3b. Accordingly, in some embodiments of the present invention a TCR, fragment or polypeptide may be defined by reference to CDR1a, CDR2a and CDR3a, and CDR1b, CDR2b and CDR3b. The variable regions of the α-chain and β-chain also comprise framework regions between the CDRs.

Accordingly, the present invention provides a TCR or a fragment comprising:
a TCR α-chain variable region comprising CDRs having the amino acid sequences i) to iii):

i)
CDR1a: DXSSTY; (SEQ ID NO: 1)

ii)
CDR2a: IFSNMDM; (SEQ ID NO: 2)

iii)
CDR3a: AETLDNYGQNFV; (SEQ ID NO: 3)

and;
a TCR β-chain variable region comprising CDRs having the amino acid sequences iv) to vi):

iv)
CDR1b: DFQATT; (SEQ ID NO: 4)

v)
CDR2b: SNEGSKA; (SEQ ID NO: 5)

vi)
CDR3b: SAVDRDEPFHSNQPQH; (SEQ ID NO: 6)

or a variant thereof in which one or two amino acids in one or more of the sequences i) to vi) are replaced with another amino acid;
where X=S or I.

Also provided is a TCR or a fragment comprising:
a TCR α-chain variable region comprising CDRs having the amino acid sequences i) iii):

i)
CDR1a: DSSSTY; (SEQ ID NO: 24)

ii)
CDR2a: IFSNMDM; (SEQ ID NO: 2)

iii)
CDR3a: AETLDNYGQNFV; (SEQ ID NO: 3)

and;
a TCR β-chain variable region comprising CDRs having the amino acid sequences iv) to vi):

iv)
CDR1b: DFQATT; (SEQ ID NO: 4)

v)
CDR2b: SNEGSKA; (SEQ ID NO: 5)

vi)
CDR3b: SAVDRDEPFHSNQPQH; (SEQ ID NO: 6)

or a variant thereof in which one or two amino acids in one or more of the sequences i) to vi) are replaced with another amino acid.

Also provided is a TCR or a fragment comprising:
a TCR α-chain variable region comprising CDRs having the amino acid sequences i) to iii):

i)
CDR1a: DISSTY; (SEQ ID NO: 25)

-continued

```
ii)
                                      (SEQ ID NO: 2)
   CDR2a: IFSNMDM;

iii)
                                      (SEQ ID NO: 3)
   CDR3a: AETLDNYGQNFV;
``` and;

a TCR β-chain variable region comprising CDRs having the amino acid sequences iv) to vi):

```
iv)
                                      (SEQ ID NO: 4)
   CDR1b: DFQATT;

v)
                                      (SEQ ID NO: 5)
   CDR2b: SNEGSKA;

vi)
                                      (SEQ ID NO: 6)
   CDR3b: SAVDRDEPFHSNQPQH;
``` or a variant thereof in which one or two amino acids in one or more of the sequences i) to vi) are replaced with another amino acid.

CDR3 of the α-chain and β-chain polypeptides are thought to be the most important CDRs for antigen recognition. Accordingly, in embodiments of the present invention a TCR, fragment or polypeptide may be defined by reference to CDR3a and CDR3b.

Accordingly, the present invention provides a TCR or a fragment thereof, optionally isolated, comprising:

a TCR α-chain variable region comprising a CDR3a having the amino acid sequence:

```
                                      (SEQ ID NO: 3)
   CDR3a: AETLDNYGQNFV,
``` or a variant thereof in which one or two amino acids are replaced with another amino acid; and;

a TCR β-chain variable region comprising a CDR3b having the amino acid sequence:

```
   CDR3b:
                                      (SEQ ID NO: 6)
   SAVDRDEPFHSNQPQH
``` or a variant thereof in which one or two amino acids are replaced with another amino acid.

The present invention also contemplates use of TCR α-chains, TCR β-chains or fragments thereof as described herein in isolation, or in combination with other molecules. For example, a TCR α-chain, TCR β-chain or fragment thereof of the invention may be useful with another TCR α-chain, TCR β-chain or fragment to form an antigen-binding molecule, e.g. a TCR. Accordingly, aspects of the present invention include a TCR or fragment defined by reference to CDRs of one of a TCR α-chain or a TCR β-chain.

Accordingly, the present invention provides TCR, or a fragment thereof, optionally isolated, comprising:

a TCR α-chain variable region comprising CDRs having the amino acid sequences i) to iii):

```
i) CDR1a:
                                      (SEQ ID NO: 1)
   DXSSTY;

ii) CDR2a:
                                      (SEQ ID NO: 2)
   IFSNMDM;

iii) CDR3a:
                                      (SEQ ID NO: 3)
   AETLDNYGQNFV;
``` or a variant thereof in which one or two amino acids in one or more of the sequences i) to iii) are replaced with another amino acid;

where X=S or I.

Also provided is a TCR, or a fragment thereof, optionally isolated, comprising:

a TCR α-chain variable region comprising CDRs having the amino acid sequences i) to iii):

```
i) CDR1a:
                                      (SEQ ID NO: 24)
   DSSSTY;

ii) CDR2a:
                                      (SEQ ID NO: 2)
   IFSNMDM;

iii) CDR3a:
                                      (SEQ ID NO: 3)
   AETLDNYGQNFV;
``` or a variant thereof in which one or two amino acids in one or more of the sequences i) to iii) are replaced with another amino acid.

Also provided is a TCR, or a fragment thereof, optionally isolated, comprising:

a TCR α-chain variable region comprising CDRs having the amino acid sequences i) to iii):

```
i) CDR1a:
                                      (SEQ ID NO: 25)
   DISSTY;

ii) CDR2a:
                                      (SEQ ID NO: 2)
   IFSNMDM;

iii) CDR3a:
                                      (SEQ ID NO: 3)
   AETLDNYGQNFV;
``` or a variant thereof in which one or two amino acids in one or more of the sequences i) to iii) are replaced with another amino acid.

Also provided is a TCR or a fragment thereof, optionally isolated, comprising:

a TCR β-chain variable region comprising CDRs having the amino acid sequences iv) to vi):

```
iv) CDR1b:
                                      (SEQ ID NO: 4)
   DFQATT;

v) CDR2b:
                                      (SEQ ID NO: 5)
   SNEGSKA;

vi) CDR3b:
                                      (SEQ ID NO: 6)
   SAVDRDEPFHSNQPQH;
``` or a variant thereof in which one or two amino acids in one or more of the sequences iv) to vi) are replaced with another amino acid.

Similarly, aspects of the present invention include an isolated TCR α-chain polypeptide or an isolated TCR β-chain polypeptide.

Accordingly, the present invention provides an isolated TCR α-chain variable region polypeptide, comprising CDRs having the amino acid sequences i) to iii):

i) CDR1a:
DXSSTY; (SEQ ID NO: 1)

ii) CDR2a:
IFSNMDM; (SEQ ID NO: 2)

iii) CDR3a:
AETLDNYGQNFV; (SEQ ID NO: 3)

or a variant thereof in which one or two amino acids in one or more of the sequences i) to iii) are replaced with another amino acid;

where X=S or I.

Also provided is an isolated TCR α-chain variable region polypeptide, comprising CDRs having the amino acid sequences i) to iii):

i) CDR1a:
DSSSTY; (SEQ ID NO: 24)

ii) CDR2a:
IFSNMDM; (SEQ ID NO: 2)

iii) CDR3a:
AETLDNYGQNFV; (SEQ ID NO: 3)

or a variant thereof in which one or two amino acids in one or more of the sequences i) to iii) are replaced with another amino acid.

Also provided is an isolated TCR α-chain variable region polypeptide, comprising CDRs having the amino acid sequences i) to iii):

i) CDR1a:
DISSTY; (SEQ ID NO: 25)

ii) CDR2a:
IFSNMDM; (SEQ ID NO: 2)

iii) CDR3a:
AETLDNYGQNFV; (SEQ ID NO: 3)

or a variant thereof in which one or two amino acids in one or more of the sequences i) to iii) are replaced with another amino acid.

Also provided is an isolated TCR β-chain variable region polypeptide comprising CDRs having the amino acid sequences iv) to vi):

iv) CDR1b:
DFQATT; (SEQ ID NO: 4)

v) CDR2b:
SNEGSKA; (SEQ ID NO: 5)

vi) CDR3b:
SAVDRDEPFHSNQPQH; (SEQ ID NO: 6)

or a variant thereof in which one or two amino acids in one or more of the sequences iv) to vi) are replaced with another amino acid.

TCRs, fragments and polypeptides according to the invention may comprise one or more CDRs which are variant CDRs of the CDRs described herein. A variant may have one or two amino acid substitutions in the CDR sequence. In some embodiments, a variant may have three or four amino acid substitutions in the CDR sequence.

The CDRs described herein may be useful in conjunction with a number of different framework regions. Amino acid sequences for TCR α-chain and TCR β-chain framework regions are well known in the art, and can for example be identified with reference to, or retrieved from, the immunogenetics (IMGT) database (http://www.imgt.org).

Peptides and Presentation

TCRs recognise antigen peptides presented by MHC molecules. Antigens are processed by the molecular machinery of antigen presenting cells (APCs) to peptides, which then become associated with MHC molecules and presented as peptide-MHC complexes at the cell surface. Different TCRs display different ability to bind to, and therefore different reactivity to, different peptide-MHC complexes. Antigen processing, loading and presentation on MHC is described in detail in, for example, Immunobiology, 5th Edn. Janeway C A Jr, Travers P, Walport M, et al. New York: Garland Science (2001), Chapter 5, hereby incorporated by reference in entirety.

The present invention is particularly concerned with T cells reactive to a HBV. Accordingly, in embodiments of the present invention the TCRs, fragments, polypeptides and cells are capable of binding to an MHC molecule presenting a peptide derived from a HBV polypeptide.

An "HBV polypeptide" as used herein refers to a polypeptide derived from a HBV virion or encoded by nucleic acid from a HBV.

"HBV" as used herein refers to any HBV. In some embodiments, a HBV is a HBV of serotype adr, adw, ayr or ayw. In some embodiments, a HBV is a HBV of genotype A, B, C, D, E, F, G, H, I or J (see e.g. Sunbul, World J Gastroenerol (2014) 20 (18): 5427-5434). In particular embodiments, the HBV genotype is B or C.

As used herein a "peptide" refers to a chain of two or more amino acid monomers linked by peptide bonds. In some embodiments a peptide may be 50 amino acids or fewer in length. A "polypeptide" as used herein refers to a chain of two or more peptides linked by peptide bonds.

In some embodiments, the HBV polypeptide may be a polypeptide encoded by the nucleic acid region of HBV encoding the virus envelope proteins, known as "env". Herein a HBV polypeptide encoded by the env region is referred to as an "Env polypeptide".

The skilled person is readily able to determine whether a given peptide or polypeptide is derived from a HBV virion, encoded by a nucleic acid from a HBV and/or encoded by the env region of a HBV for example by protein BLAST (BLASTP) analysis of the amino acid sequence of the peptide or polypeptide.

In some embodiments, the HBV polypeptide may be a polypeptide encoded by nucleic acid encoding surface (S) region of an HBV Env polypeptide (described, for example, in Tan et al., J Virol (2014) 88 (2): 1332-1341, hereby incorporated by reference in its entirety). Herein a HBV polypeptide encoded by nucleic acid encoding the S region of an Env polypeptide is referred to as an "S polypeptide".

In some embodiments, the peptide recognised by a TCR, fragment, polypeptide or cell according to the present invention is a peptide of an Env polypeptide and/or an S polypeptide. In some embodiments, the peptide comprises a sequence of amino acids comprising amino acids at positions 171-180 of HBV Env polypeptide, wherein the residues of Env are numbered relative to Env from HBV genotype B.

In some embodiments, the peptide comprises, or consists of, the sequence of amino acids comprising positions 171-180 of HBV Env polypeptide, FLGPLLVLQA (SEQ ID NO: 19) or LLGPLLVLQA (SEQ ID NO: 20), or variant thereof having one or two or three amino acid substitutions in the amino acid sequence. In some embodiments, the peptide additionally comprises 1, 2, 3, 4, 5 amino acids at one or both ends of the amino acid sequence. In some embodiments, the peptide additionally comprises 1-2, 1-3, 1-4, or 1-5 amino acids at one or both ends of the amino acid sequence.

In some embodiments, a substitution in the amino acid sequence is not at position one of SEQ ID NO: 19 or 20. In some embodiments, a substitution in the amino acid sequence is not at position ten of SEQ ID NO: 19 or 20.

In some embodiments, the peptide is one of 5-15, 5-14, 5-13, 5-12, 5-11, 5-10, 5-9 or 5-8 amino acids in length. In some embodiments, the peptide is one of 5-15, 6-15, 7-15, 8-15, 9-15, 10-15, 11-15 or 12-15 amino acids in length. In some embodiments, the peptide is one of 5, 6, 7, 8, 9, 10, 11, 12, 13, 14, or 15 amino acids in length.

In embodiments of the present invention the peptide is presented by an MHC molecule. In some embodiments, the MHC molecule is an MHC class I molecule.

MHC class I molecules are heterodimers of an α-chain and a β2-microglobulin. The α-chain has three domains designated α1, α2 and α3. The α1 and α2 domains together form the groove to which the peptide presented by the MHC class I molecule binds, to form the peptide-MHC complex. MHC class I α-chains are polymorphic, and different α-chains are capable of binding and presenting different peptides. In humans MHC class I α-chains are encoded by human leukocyte antigen (HLA) genes.

In embodiments according to the present invention a TCR, fragment, polypeptide or cell is capable of binding to a peptide derived from a HBV polypeptide presented by an MHC class I molecule.

In some embodiments, the MHC class I molecule comprises an α-chain encoded at the HLA-C locus. In some embodiments, the α-chain is encoded by an HLA-C allele which is a member of allele group HLA-Cw*08. In some embodiments, the α-chain is encoded by HLA-Cw*0801. In some embodiments, the α-chain is not encoded by HLA-Cw*0801.

It will be understood that the TCR, fragment, polypeptide or cell according to the present invention is capable of binding to an HBV peptide as described herein presented by an MHC class I molecule as described herein. In particular embodiments, the present invention is directed to a TCR, fragment, polypeptide or cell which is capable of binding to one or more of:

(i) a peptide derived from a HBV polypeptide presented by an MHC class I molecule comprising an α-chain encoded by an HLA-Cw*08 allele, optionally wherein the HLA-Cw*08 allele is one of HLA-Cw*0801, or wherein the HLA-Cw*08 allele is not HLA-Cw*0801.

(ii) a peptide derived from a HBV polypeptide presented by an MHC class I molecule wherein the peptide comprises, or consists of, the sequence of amino acids comprising positions 171-180 of HBV Env polypeptide, FLGPLLVLQA (SEQ ID NO: 19) or LLGPLLVLQA (SEQ ID NO: 20), or a variant thereof having one or two or three amino acid substitutions in the amino acid sequence.

(iii) a peptide comprising, or consisting of, the sequence of amino acids comprising positions 171-180 of HBV Env polypeptide, FLGPLLVLQA (SEQ ID NO: 19) or LLGPLLVLQA (SEQ ID NO: 20), or a variant thereof having one or two or three amino acid substitutions in the amino acid sequence presented by an MHC class I molecule comprising an α-chain encoded by an HLA-Cw*08 allele, optionally wherein the HLA-Cw*08 allele is one of HLA-Cw*0801, or wherein the HLA-Cw*08 allele is not HLA-Cw*0801.

The present invention also provides a complex, optionally an in vitro complex, comprising a TCR, fragment, polypeptide or cell according to the present invention and a HBV peptide as described herein. In some embodiments, the complex comprises an MHC class I molecule as described herein.

Recombinant TCRs, Fragments, Polypeptides and Cells

In various aspects, the present invention provides non-naturally occurring products. Such products may be variously referred to as recombinant, artificial, non-native or man-made products.

In one aspect, the present invention provides exogenous TCRs, fragments, polypeptides, nucleic acids and cells. An exogenous TCR, fragment, polypeptide, nucleic acid or cell according to the present invention has a structure as described herein.

"Exogenous" as used herein generally means not endogenous. In the context of a cell, an exogenous TCR, fragment, or polypeptide according to the invention may refer to a TCR, fragment or polypeptide which is not encoded by nucleic acid of that cell, e.g. prior to any introduction of nucleic acid encoding the exogenous TCR, fragment or polypeptide into the cell. An exogenous nucleic acid refers to a nucleic acid not present in that cell e.g. prior to any introduction of the nucleic acid into the cell.

In the context of a subject, an exogenous TCR, fragment, or polypeptide may refer to a TCR, fragment, or polypeptide which is not present in the subject or encoded by nucleic acid, e.g. of the genome, of the subject, prior to any introduction of the TCR, fragment, polypeptide, or nucleic acid encoding the exogenous TCR, fragment or polypeptide into the subject. An exogenous nucleic acid refers to a nucleic acid not present in that subject, e.g. prior to any introduction of the nucleic acid into the subject. An exogenous cell refers to a cell not present in that subject, e.g. prior to any introduction of a cell and/or nucleic acid into the subject.

In one aspect, the present invention provides nucleic acid encoding a TCR, fragment or polypeptide according to the present invention. In some embodiments, the nucleic acid is purified or isolated, e.g. from other nucleic acid, or naturally-occurring biological material.

In some embodiments, a nucleic acid according to the invention may comprise one or more of SEQ ID NOs: 7 to 18 (FIG. 11), or a coding sequence which is degenerate as a result of the genetic code, or may comprise a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

In some embodiments, the nucleic acid comprises (a) a nucleic acid sequence encoding a TCR α-chain comprising a variable region and a constant region. In some embodiments, the nucleic acid comprises (b) a nucleic acid sequence encoding a TCR β-chain comprising a variable region and a constant region. In some embodiments, the nucleic acid comprises (a) a nucleic acid sequence encoding a TCR α-chain comprising a variable region and a constant region, and (b) a nucleic acid sequence encoding a TCR β-chain comprising a variable region and a constant region.

In some embodiments, it may be desirable to express TCR α- and β-chains according to the invention as a fusion protein. This may for example be desirable to achieve similar levels of protein expression for each chain. Accordingly, in some embodiments, the nucleic acid additionally comprises (c) a nucleic acid sequence encoding a linker sequence. A "linker sequence" as used herein refers to a sequence of amino acids for linking expressed peptide or polypeptide sequences. In the present invention, a linker sequence is for linking TCR α- and β-chains.

In some embodiments, it may be desirable to separate TCR α- and β-chains expressed as a fusion protein. In some embodiments, this may be achieved by providing for cleaving the fusion protein between the TCR α- and β-chains.

Accordingly, in some embodiments, the linker sequence may be a cleavable linker. That is, the linker sequence may comprise a sequence of amino acids which is capable of being cleaved. For example, the linker sequence may comprise a sequence capable of acting as a substrate for an enzyme capable of cleaving peptide bonds—i.e. a cleavage site. Many such cleavage sites are known to and can be employed by the person skilled in the art of molecular biology. In some embodiments, the cleavable linker may comprise an autocleavage site. Autocleavage sites are automatically cleaved without the need for treatment with enzymes. An example of an autocleavage site is the 2A sequence from Picornavirus "NPGP", which is cleaved at "G/P". This autocleavage sequence is herein referred to as "Picornavirus 2A (P2A)". A linker sequence comprising P2A is herein referred to as a P2A linker.

In it will be appreciated that where it is desired for TCR α- and β-chains to be expressed as a single polypeptide joined by a linker sequence, the nucleic acid sequences encoding the TCR α- and β-chains and linker must be provided in the same reading frame.

Nucleic acids according to the present invention may comprise sequences (a) and (b), and optionally (c), in particular orientations in the nucleic acid. That is, the sequences may be provided in a particular order. The particular 5' to 3' order of sequences (a) and (b), and optionally (c) may influence e.g. transcription, post-transcriptional processing, translation, post-translational processing, folding, associations, stability, degradation, trafficking, and/or functional properties of the nucleic acid/expressed product.

In some embodiments of the nucleic acid according to the invention sequences (a) and (b) are provided in the 5' to 3' orientation: 5'-(b)-(a)-3'. In some embodiments, sequences (a) and (b) are provided in the 5' to 3' orientation: 5'-(a)-(b)-3'. In some embodiments, sequences (a), (b) and (c) are provided with the 5' to 3' orientation: 5'-(b)-(c)-(a)-3'. In some embodiments, sequences (a), (b) and (c) are provided with the 5' to 3' orientation: 5'-(a)-(c)-(b)-3'.

In some embodiments, the nucleic acids encode one or more structural features for increasing and/or stabilising association between expressed TCR α- and β-chains. In some embodiments, the feature may be a particular amino acid or sequence of amino acids. In some embodiments, the nucleic acid may encode one or more non-native cysteine residues for forming one or more disulphide bonds between the TCR α- and β-chains. In some embodiments, the nucleic acid may encode one or more non-native cysteine residues in the constant region of the TCR α- and/or β-chains.

One aspect of the present invention provides a vector comprising a nucleic acid according to the present invention.

A "vector" as used herein is a nucleic acid (DNA or RNA) used as a vehicle to transfer exogenous nucleic acid into a cell. The vector may be an expression vector for expression of the nucleic acid in the cell. Such vectors may include a promoter sequence operably linked to the nucleic acid encoding the sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, DNA vectors, mRNA vectors, viral vectors (e.g. gammaretroviral vectors, lentiviral vectors, adenovirus vectors), transposon-based vectors, and artificial chromosomes (e.g. yeast artificial chromosomes), e.g. as described in Maus et al., Annu Rev Immunol (2014) 32:189-225, which is hereby incorporated by reference in its entirety.

In some embodiments according to the invention, the viral vector may be a lentiviral, retroviral, adenoviral, or Herpes Simplex Virus vector.

In this specification the term "operably linked" may include the situation where a selected nucleic acid sequence and regulatory nucleic acid sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. Where appropriate, the resulting transcript may then be translated into a desired polypeptide.

The present invention also provides a method for producing a TCR, fragment or polypeptide according to the invention, comprising introducing into a cell a vector according to the invention and culturing the cell under conditions suitable for expression of the vector by the cell.

Any cell suitable for the expression of polypeptides may be used for producing TCRs, fragments and polypeptides according to the invention. The cell may be a prokaryote or eukaryote. Suitable prokaryotic cells include *E. coli*. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the TCR, fragment or polypeptide into the media.

Methods of producing a TCR, fragment or polypeptide according to the invention may involve culture or fermentation of a cell modified to express the TCR, fragment or polypeptide. The culture or fermentation may be performed in a bioreactor provided with an appropriate supply of nutrients, air/oxygen and/or growth factors. Proteins can be extracted from the cells, culture media or fermentation broth, and separated isolate the TCR, fragment or polypeptide according to the invention. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the TCR, fragment or polypeptide, the TCR, fragment or polypeptide is preferably isolated. Any suitable method for separating polypeptides from cell culture known in the art may be used. In order to isolate the TCR, fragment or polypeptide from a culture, it may be necessary to first separate the cultured cells from media containing the TCR, fragment or polypeptide. If the TCR, fragment or polypeptide of interest is secreted from the cells, the cells may be separated from the culture media that contains the secreted polypeptide/protein by centrifugation. If the TCR, fragment or polypeptide collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the TCR, fragment or polypeptide from the supernatant or culture medium, which may contain other protein and non-protein components. A common approach to separating polypeptide components from a supernatant or culture medium is by precipitation. Polypeptides of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides are known in the art, for example ion exchange chromatography and size chromatography. These may be used as an alternative to precipitation, or may be performed subsequently to precipitation.

Once the TCR, fragment or polypeptide has been isolated from culture it may be necessary to concentrate the protein. A number of methods for concentrating a protein of interest are known in the art, such as ultrafiltration or lyophilisation.

Also provided by the present invention is a method for producing a cell, comprising introducing a nucleic acid or vector according to the present invention into a cell. In some embodiments, the method additionally comprises culturing the cell under conditions suitable for expression of the nucleic acid or vector by the cell. In some embodiments, the method is an in vitro method.

In some embodiments, introducing an isolated nucleic acid or vector according to the invention comprises transduction, e.g. retroviral transduction. Accordingly, in some embodiments the isolated nucleic acid or vector is comprised in a viral vector, or the vector is a viral vector. In some embodiments, the method comprises introducing a nucleic acid or vector according to the invention by electroporation, for example as described in Koh et al., Molecular Therapy—Nucleic Acids (2013) 2, e114, which is hereby incorporated by reference in its entirety.

In some embodiments, the method is a method for producing a modified immune cell, wherein the immune cell can be a T cell, a Natural Killer Cells, a Dendritic Cell, or a Macrophage, optionally the immune cell is a T cell. In some embodiments, the T cell is a CD3+ T cell. In some embodiments, the T cell is a CD3+, CD8+ T cell. In some embodiments, the T cell is a cytotoxic T cell. Accordingly, in some embodiments the method comprises introducing a nucleic acid or vector according to the present invention into a CD3+ cell. In some embodiments, the method comprises introducing a nucleic acid or vector according to the present invention into a CD3+, CD8+ cell.

The present invention also provides cells obtained or obtainable by the methods for producing a cell according to the present invention.

In some embodiments, the method is a method for producing a HBV reactive T cell. In embodiments herein, a "HBV reactive" T cell is a cell which displays certain functional properties of a T cell in response to a cell infected with HBV or comprising or expressing an HBV peptide. In some embodiments, the properties are functional properties associated with effector T cells, e.g. cytotoxic T cells. In some embodiments, a HBV reactive T cell may display one or more of the following properties: cytotoxicity to a cell infected with HBV or comprising or expressing an HBV peptide; proliferation, increased IFNγ expression, increased CD107a expression, increased IL-2 expression, increased TNFα expression, increased perforin expression, increased granzyme expression and/or increased FAS ligand (FASL) expression in response to contact with a cell infected with HBV or comprising or expressing an HBV peptide.

Antigen-specific CD8+ T cells can be identified based by flow cytometric assay for degranulation, e.g. as described in Betts et al., J Immunol Methods 2003 281 (1-2):65-78, and discussed in Zaritskaya et al. Expert Rev Vaccines (2011), 9 (6):601-616, both hereby incorporated by reference in their entirety.

In some embodiments, the cell infected with HBV may be infected with HBV of genotype A, B, C, D, E, F, G, H, I or J. In particular embodiments, the HBV genotype is B or C. In some embodiments, the cell comprises or expresses an HBV peptide according to any embodiment of a HBV peptide described herein.

In some embodiments, the cell infected with HBV or comprising or expressing an HBV peptide may comprise an MHC class I molecule comprising an MHC class I α-chain encoded by an HLA-C allele, optionally wherein the HLA-C allele is a member of allele group HLA-Cw*08, optionally wherein the α-chain is encoded by HLA-Cw*0801, or wherein the α-chain is not encoded by HLA-Cw*0801. In some embodiments, the cell infected with HBV or comprising or expressing an HBV peptide may comprise nucleic acid encoding an HLA-C allele, optionally wherein the HLA-C allele is a member of allele group HLA-Cw*08, optionally wherein the HLA-C allele is HLA-Cw*0801, or wherein the HLA-C allele is not HLA-Cw*0801.

Methods for investigating cytotoxicity and/or expression may include the use of HLA-matched antigen presenting cells pulsed with HBV peptide, for example as described in Example 6 herein.

As used herein, "cytotoxicity" refers to cell killing. Cytotoxicity of a T cell to a given target cell (i.e. a cell infected with HBV or comprising or expressing an HBV peptide) can be investigated, for example, using any of the methods reviewed in Zaritskaya et al. Expert Rev Vaccines (2011), 9 (6):601-616, hereby incorporated by reference in its entirety. One example of an assay for cytotoxicity of a T cell for to a target cell is the $^{51}$Cr release assay, in which target cells are treated with $^{51}$Cr, which they internalise. Lysis of the target cells by T cells results in the release of the radioactive $^{51}$Cr into the cell culture supernatant, which can be detected.

Herein, "expression" of IFNγ, CD107a, IL-2, TNFα, perforin, granzyme and/or FASL may refer to gene expression or protein expression. Gene expression can be measured by a various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

"Increased expression" refers to a level of expression which is greater than the level of expression of the gene/protein by a T cell which has not been contacted with a cell infected with HBV or comprising or expressing an HBV peptide, or the level of expression by a T cell in response to contact with a cell which is not infected with HBV, or cell not comprising or expressing an HBV peptide as described herein. In some embodiments, the increased gene or protein expression may be one of more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times the level of expression by a T cell which has not been contacted with a cell infected with HBV or comprising or expressing an HBV peptide, or the level of expression by a T cell in response to contact with a cell which is not infected with HBV, or cell not comprising or expressing an HBV peptide as described herein.

Medical Uses and Methods of Treatment and Prophylaxis

The TCR, fragment, nucleic acid, vector, polypeptide or cell according to the present invention finds use in therapeutic and prophylactic methods.

Accordingly, in one aspect the present invention provides a TCR, fragment, nucleic acid, vector, polypeptide, cell or pharmaceutical composition according to the present invention for use in a method of treating or preventing a disease or disorder.

In another aspect, the present invention provides the use of a TCR, fragment, nucleic acid, vector, polypeptide, cell or pharmaceutical composition according to the present invention in the manufacture of a medicament for treating or preventing a disease or disorder.

In another aspect, the present invention provides a method of treating or preventing a disease or disorder, comprising administering to a subject a therapeutically or prophylactically effective amount of TCR, fragment, nucleic acid, vector, polypeptide, cell or pharmaceutical composition according to the present invention.

In particular, the TCR, fragment, nucleic acid, vector, polypeptide, cell or pharmaceutical composition according to the present invention finds use to prevent or treat a disease which is caused or exacerbated by HBV infection, or a disease or disorder for which HBV infection is a risk factor.

Diseases and disorders which are caused/exacerbated by HBV infection are described in Liang, Hepatology (2009), 49 (5 Suppl): S13-S21, and include acute hepatitis (including fulminant hepatic failure), chronic hepatitis, cirrhosis, liver cancer such as hepatocellular carcinoma (HCC), or pancreatic cancer. Diseases and disorders for which HBV infection is a risk factor include necrotizing vasculitis and nephropathy such as membranous glomerulonephritis (MGN).

Administration of a TCR, fragment, nucleic acid, vector, polypeptide or cell according to the invention is preferably in a "therapeutically effective" or "prophylactically effective" amount, this being sufficient to show benefit to the subject. The actual amount administered, and rate and time-course of administration, will depend on the nature and severity of the disease or disorder. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

In embodiments of the present invention, a method of treatment or prophylaxis may comprise adoptive transfer of T cells. Adoptive T cell transfer generally refers to a process by which T cells are obtained from a subject, typically by drawing a blood sample from which T cells are isolated. The T cells are then typically treated or altered in some way, and either to the same subject or to a different subject. The treatment is typically aimed at providing a T cell population with certain desired characteristics to a subject, or increasing the frequency of T cells with such characteristics in that subject. Adoptive transfer of virus specific T cells is described, for example, in Cobbold et al., (2005) J. Exp. Med. 202: 379-386 and Rooney et al., (1998), Blood 92:1549-1555, hereby incorporated by reference in its entirety.

In the present invention, adoptive transfer is performed with the aim of introducing, or increasing the frequency of, HBV reactive T cells in a subject, in particular HBV reactive CD8+ T cells and/or CD4+ T cells.

Accordingly, in one aspect, the present invention provides a method of treating or preventing a disease or disorder in a subject, comprising:
(a) isolating at least one T cell from a subject;
(b) modifying the at least one T cell to express or comprise a TCR, fragment, nucleic acid, vector, or polypeptide according to the present invention, and;
(c) administering the modified at least one T cell to a subject.

In some embodiments, the subject from which the T cell is isolated is the subject administered with the modified T cell.

The at least one T cell modified according to the present invention can be modified according to methods well known to the skilled person. The modification may comprise nucleic acid transfer for permanent or transient expression the transferred nucleic acid.

Any suitable genetic engineering platform may be used to modify a T cell according to the present invention. Suitable methods for modifying a T cell include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, incorporated by reference hereinabove.

In some embodiments the method may comprise one or more of the following steps: taking a blood sample from a subject; isolating at least one T cell from the blood sample; culturing the at least one T cell in in vitro or ex vivo cell culture; introducing into the at least one T cell a TCR, fragment, nucleic acid, vector, or polypeptide according to the present invention, thereby modifying the at least one T cell; collecting the at least one T cell; mixing the modified T cell with an adjuvant, diluent, or carrier; administering the modified T cell to a subject.

The skilled person is able to determine appropriate reagents and procedures for adoptive transfer of HBV reactive T cells according to the present invention for example by reference to Qasim et al., Journal of Hepatology (2015) 62: 486-491, which is incorporated by reference in its entirety.

In a related aspect, the present invention provides a method of preparing a modified T cell, the method comprising introducing into a T cell a TCR, fragment, nucleic acid, vector, or polypeptide according to the present invention, thereby modifying the at least one T cell. The method is preferably performed in vitro or ex vivo.

In one aspect, the present invention provides a method of treating or preventing a disease or disorder in a subject, comprising:
(a) isolating at least one T cell from a subject;
(b) introducing into the at least one T cell the isolated nucleic acid or vector according to the present invention, thereby modifying the at least one T cell; and
(c) administering the modified at least one T cell to the subject.

In embodiments according to the present invention the subject is preferably a human subject. In some embodiments, the subject to be treated according to a therapeutic or prophylactic method of the invention herein is selected based on HLA genotype. In some embodiments, the subject has an HLA allele encoding an MHC class I α-chain which in the context of an MHC class I molecule is capable of presenting an HBV peptide as described herein. In some embodiments, the subject has an HLA-C genotype comprising an HLA-Cw*08 allele. In some embodiments, the HLA-Cw*08 allele is HLA-Cw*0801. In some embodiments, the HLA-Cw*08 allele is not HLA-Cw*0801. In some embodiments, the subject is of Asian ethnicity. In some embodiments, the patient is of Southeast Asian ethnicity.

In embodiments according to the present invention, a subject may be selected for a treatment of a disease or disorder caused or exacerbated by HBV infection, or a disease or disorder for which HBV infection is a risk factor based on characterisation for certain markers of such disease/disorder, e.g. HBV infection. A subject may have been diagnosed with the disease or disorder requiring treatment, or be suspected of having such a disease or disorder.

In embodiments according to the present invention, a subject may be selected for a prophylactic method herein for the prevention of a disease or disorder caused or exacerbated by HBV infection, or a disease or disorder for which HBV infection is a risk factor based on characterisation for certain risk factors for HBV infection.

In embodiments according to various aspects of the present invention, treating or preventing a disease or disorder according to the present invention may comprise combination therapy. In such embodiments, a TCR, fragment, nucleic acid, vector, polypeptide, cell or pharmaceutical composition according to the present invention may be administered as part of a course comprising further intervention.

In some embodiments, the method comprises intervention—e.g. through administration of a suitable agent—for the prevention or treatment of HBV infection, or a disease or disorder caused or exacerbated by HBV infection. Prophylactic intervention may comprise vaccination, e.g. with hepatitis B vaccine described in Weekly epidemiological record 40 (84): 405-420 (2009). Suitable therapeutic agents include agents, such as those described in the WHO Guidelines for the prevention, care and treatment of persons with chronic hepatitis B infection, March 2015, ISBN 9789241549059, and Alberti and Caporaso, Dig Liver Dis, 2011 43 Suppl 1: S57-63, which are both hereby incorporated by reference in their entirety. In particular, the present invention contemplates use of antiviral agents such as lamivudine (Epivir), adefovir (Hepsera), tenofovir (Viread), telbivudine (Tyzeka) and entecavir (Baraclude), and combinations thereof, and also interferon alpha-2a and PEGylated interferon alpha-2a.

In some embodiments, the method comprises therapeutic or prophylactic intervention for the treatment or prevention of a cancer, such as a hepatic cancer, e.g. hepatocellular carcinoma.

Patient Selection

The present invention also provides methods for identifying a subject for therapeutic or prophylactic treatment according to the invention.

In one aspect, a method for identifying a subject for therapeutic or prophylactic treatment comprises determining the HLA type for a subject. In particular embodiments the method comprises determining the HLA-C genotype for the subject.

HLA typing can be performed by various methods well known to the skilled person, such as by sequencing the HLA gene or genes to by typed, and comparing the DNA sequence to sequences for known HLA alleles.

In some embodiments, a subject determined to have a HLA-Cw*08 allele is identified as being a subject suitable for therapeutic or prophylactic treatment according to the invention. In some embodiments, the HLA-Cw*08 allele is HLA-Cw*0801. In some embodiments, the HLA-Cw*08 allele is not HLA-Cw*0801.

In one aspect, a method for identifying a subject for therapeutic or prophylactic treatment comprises determining whether the subject is infected with, or is at risk of infection by, HBV, e.g. HBV genotype A, B, C, D, E, F, G, H, I or J. In particular embodiments, the HBV genotype is B or C.

HBV infection can be determined by various methods well known to the skilled person, reviewed, for example, in Aspinall et al., Occup Med (Lond) (2011) 61 (8): 531-540, which is hereby incorporated by reference in its entirety. Diagnostic tests frequently used in the diagnosis of HBV infection include tests for the presence of one or more of hepatitis B surface antigen, hepatitis B surface antibody, and hepatitis B core antibody in the blood. Other methods include tests for the presence of HBV DNA in clinical samples.

Diagnostic Methods

In a further aspect, the present invention provides a method for diagnosing HBV infection in a subject, comprising detecting the presence of a TCR, fragment, polypeptide, nucleic acid, vector, complex or cell according to the present invention.

In some embodiments, detection is in a sample, e.g. a blood or tissue sample. In some embodiments, the sample may comprise or may be derived from: a quantity of blood; a quantity of serum derived from the subject's blood which may comprise the fluid portion of the blood obtained after removal of the fibrin clot and blood cells; a tissue sample or biopsy; or cells isolated from the subject.

In some embodiments, the sample has been obtained from the subject. In some embodiments, the method is performed in vitro.

In some embodiments, the method comprises a step of obtaining a sample from the subject, and analysing the sample the detect the presence of a TCR, fragment, polypeptide, nucleic acid, vector, complex or cell according to the present invention.

In particular embodiments, the method is not practised on the human or animal body.

Compositions

The present invention also provides compositions comprising a TCR, fragment, nucleic acid, vector, polypeptide or cell according to the present invention. In some embodiments, the composition is a pharmaceutical composition. In some embodiments, the composition is a composition suitable for use in research, therapy, prophylaxis and/or diagnosis.

In some embodiments, a TCR, fragment, nucleic acid, vector, polypeptide or cell according to the present invention preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for administration by a number of routes. The medicaments and compositions may be formulated in fluid or solid (including powder) form. The route for administration may be topical, parenteral, systemic, intravenous, intra-arterial, intramuscular, intrathecal, intraocular, subcutaneous, oral or transdermal. In some embodiments, administration may include injection. Injectable formulations may comprise the selected agent in a sterile or isotonic medium.

In one aspect of the present invention a kit of parts is provided. The kit of parts comprises a predetermined quantity of a TCR, fragment, nucleic acid, vector, polypeptide, cell or pharmaceutical composition according to the present invention.

In some embodiments, the kit may include instructions for using the TCR, fragment, nucleic acid, vector, polypeptide, cell or pharmaceutical composition in a method as described herein. For example, in some embodiments the kit may include instructions for administration of the TCR, fragment, nucleic acid, vector, polypeptide, cell or pharmaceutical composition to a patient in order to treat or prevent a disease or disorder which is caused or exacerbated by HBV infection, or a disease or disorder for which HBV infection is a risk factor.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIG. 3. Graphs showing CD8+ and CD107a+ expression by E35-stimulated T cells after expansion in vitro, compared to unstimulated control.

FIG. 11. Amino acid and nucleic acid sequences for the complementarity determining regions of the TCR α and TCR β chains. Nucleic acid sequences determined by sequence analysis and following codon optimisation are shown.

FIG. 16. Schematic representations of Vα-P2A-V/β and Vβ-P2A-Vα constructs.

FIG. 17. Graphs showing Vb expression and E34 pentamer binding by CD8+ T cells transduced with Vα-P2A-Vβ and Vβ-P2A-Vα constructs.

EXAMPLES

The inventors describe in the following Examples the identification and characterisation of HBV reactive T cell clone, including analysis of the epitope which the TCR binds, presentation of the HBV peptide by MHC class I, cloning and sequence determination of the TCR, production and optimisation of TCR constructs, generation of T cells engineered to express the TCR, and functional characterisation of T cells expressing the TCR.

Example 1: Screening of In Vitro Expanded Cells

Blood was obtained from healthy donors having resolved acute Hepatitis B infection. PBMCs from donors were isolated by Ficoll-Hypaque density gradient centrifugation (Sigma Chemical Co., St. Louis, Mo.), and re-suspended in AIM-V medium (Gibco-BRL Laboratories, Gaithersburg, Md.) with 2% human AB serum.

A library of short peptides overlapping by 10 amino acid residues and covering the whole HBV proteome sequence was prepared. In particular, the envelope protein was pooled in a 9-by-9 matrix containing nine peptides/pool and polymerase protein formed a 14-by-12 matrix containing 12 or 14 peptides/pool.

PBMCs were aliquoted into plates and expanded in vitro with the synthetic peptides described above for 10 days.

Figure 1:
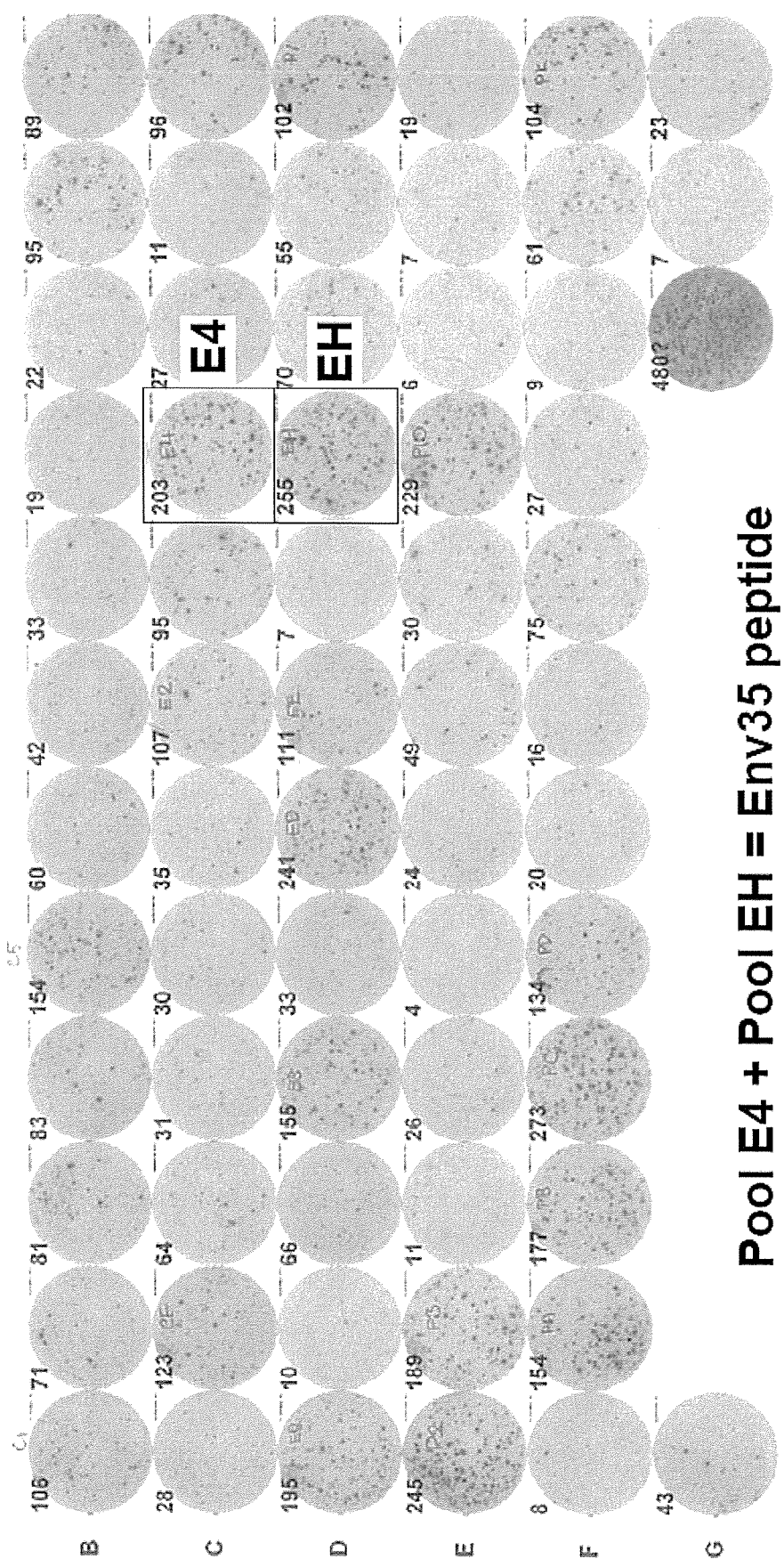
FIG. 1. Photograph showing results of ELISPOT analysis for IFNγ production by T cells in response to stimulation with HBV peptides.

The peptide pools were then used to stimulate and screen for specific T cell clones. PBMCs were incubated for 1 h at 37° C., then washed and co-cultured with another 4-fold of PBMC in AIM-V medium with 2% human AB serum and 20 U/ml of IL-2 (R&D Systems, Abingdon, United Kingdom). HBV-specific T cell responses were analyzed by ELISPOT assay after expansion, as described in Tan et al., J Virol (2014), 88 (2): 1332-1341, and wells with a positive response were identified (FIG. 1).

A T cell clone was identified as having high IFNγ production specific to peptide 35 of HBV Genotype C (herein referred to as E35 Gen C). E35 HBV genotype C peptide has the amino acid sequence FLGPLLVLQA (SEQ ID NO: 19), and E35 HBV genotype B peptide has the amino acid sequence LLGPLLVLQA (SEQ ID NO: 20) (see FIG. 2).

Example 2: Specificity Test to Confirm ELISPOT Response

Figure 4:
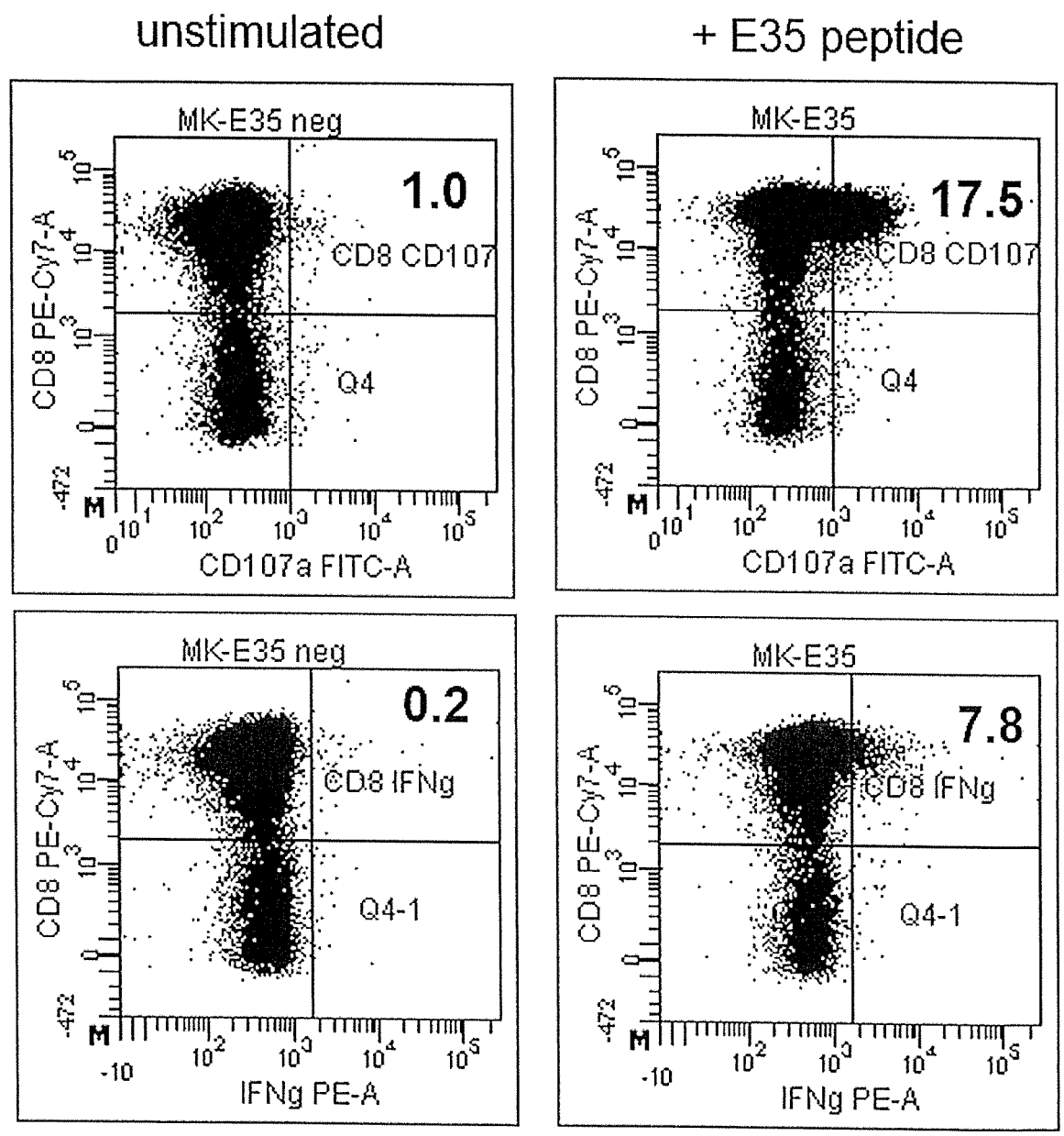
FIG. 4. Graphs showing CD8+, CD107a+ and IFNγ expression by T cells after restimulation, compared to unstimulated control.

The identified E35-specific T cells were stimulated with E35 Gen C peptide (i.e. FLGPLLVLQA; E35 Gen C) for 5 hours to confirm specificity by cytotoxic degranulation assay. Cells were re-stimulated with 2 µg/ml of E35 Gen C peptide in the presence of CD107a and Brefeldin A. Expanded cells were labelled with Cy-chrome-conjugated anti-CD8+ and CD107a-PE antibody (BD Pharmingen, San Diego, Calif.) on ice for 15 min. Cells were then washed, fixed and permeabilised by treatment with Cytofix/Cytoperm (BD Biosciences) according to the manufacturer's instruction. Cells were then stained with anti-IFNγ PE (BD Biosciences) for 30 min, washed and re-suspended in PBS before acquired by FACS and analysed using FACs Diva software. FIG. 3 shows CD8+ and CD107a+ expression by E35 GenC-stimulated T cells after in vitro expansion, compared to expression by unstimulated control PBMCs. FIG. 4 shows CD8+ and CD107a+, and IFNγ expression following restimulation with peptide compared to expression by unstimulated control PBMCs. A clear increase in degranulation activity was detected, as demonstrated by increased frequency of CD8+ CD107+ T cell population.

Figure 2:
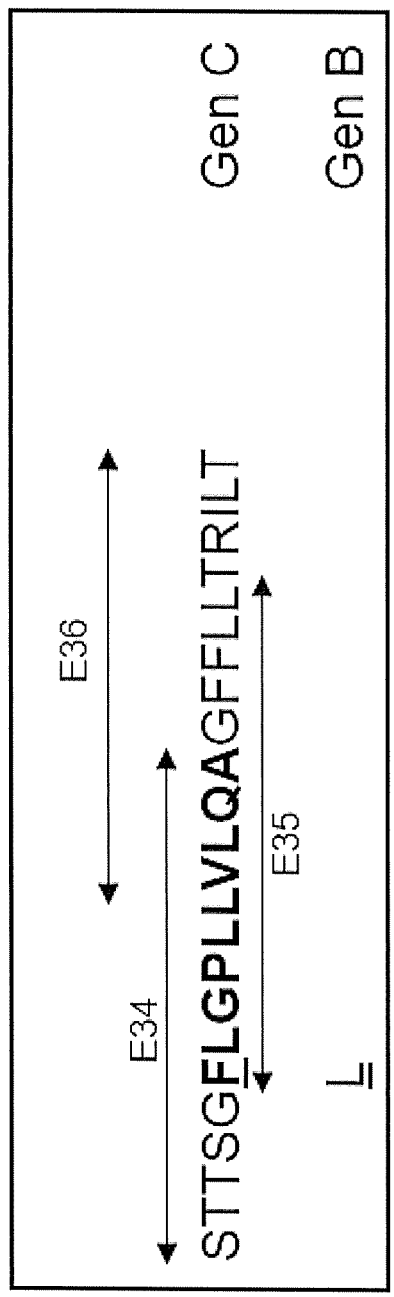
FIG. 2. Schematic representation of HBV peptides E34, E35 and E36, of HBV genotypes B and C.

Because infection by HBV genotypes B and C is particularly prevalent in Asia, responses of the T cell clone to stimulation with overlapping peptides having sequences corresponding to genotypes B and C in the region of and flanking peptide E35 were investigated (see FIG. 2).

E34 HBV genotype C peptide has the sequence STTSGFLGPLLVLQA (SEQ ID NO:21). E34 HBV genotype B peptide has the sequence STTSGLLGPLLVLQA (SEQ ID NO: 22). E36 corresponds to HBV genotypes B and C, and has the sequence VLQAGFFLLTRILT (SEQ ID NO: 23).

Figure 5:
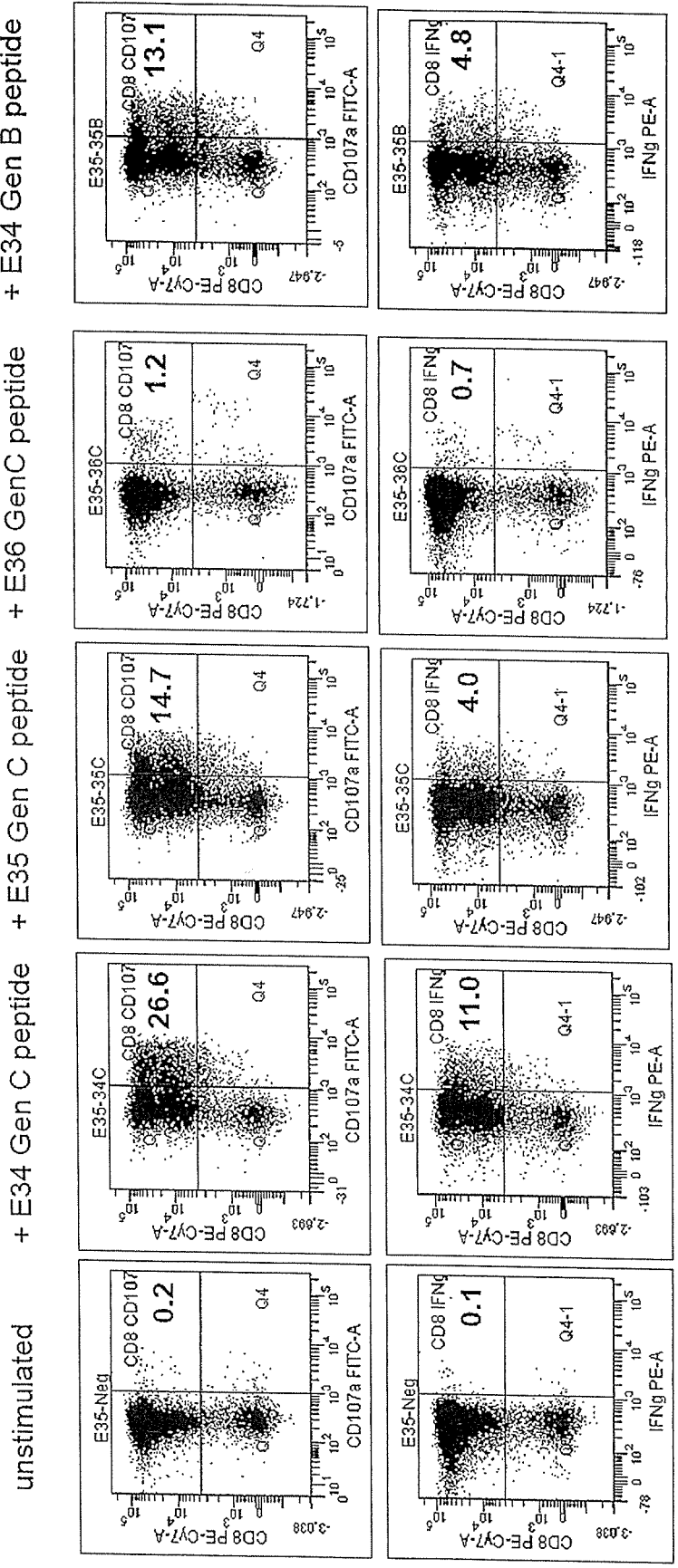
FIG. 5. Graphs showing CD107a+ and IFNγ expression by T cells following stimulation with different HBV Env peptides as compared to unstimulated control.

2 µg/ml of peptides were added together with CD107a and Brefeldin A. After 5 hours incubation, cells were stained for surface CD8 PE-Cy7-A, CD107a FITC-A and IFN-g PE-A, later acquired by FACS. The results are shown in FIG. 5. The T cell clone shows highest IFNγ production in response to stimulation with HBV genotype C E34 peptide (STTSGFLGPLLVLQ), with a lesser, but still significant, response observed in response to stimulation with HBV genotype C peptide E35 (FLGPLLVLQAGFFLL) and HBV genotype B E34 peptide (LLGPLLVLQAGFFLL).

To further investigate the fine specificity of the epitope recognition, a panel of 9- to 11-mers specific to the overlapping region of E34 and E35 (FIG. 6A) were designed to test the T cell clone after a second round of re-stimulation according to same protocol as described above.

Figure 6B:
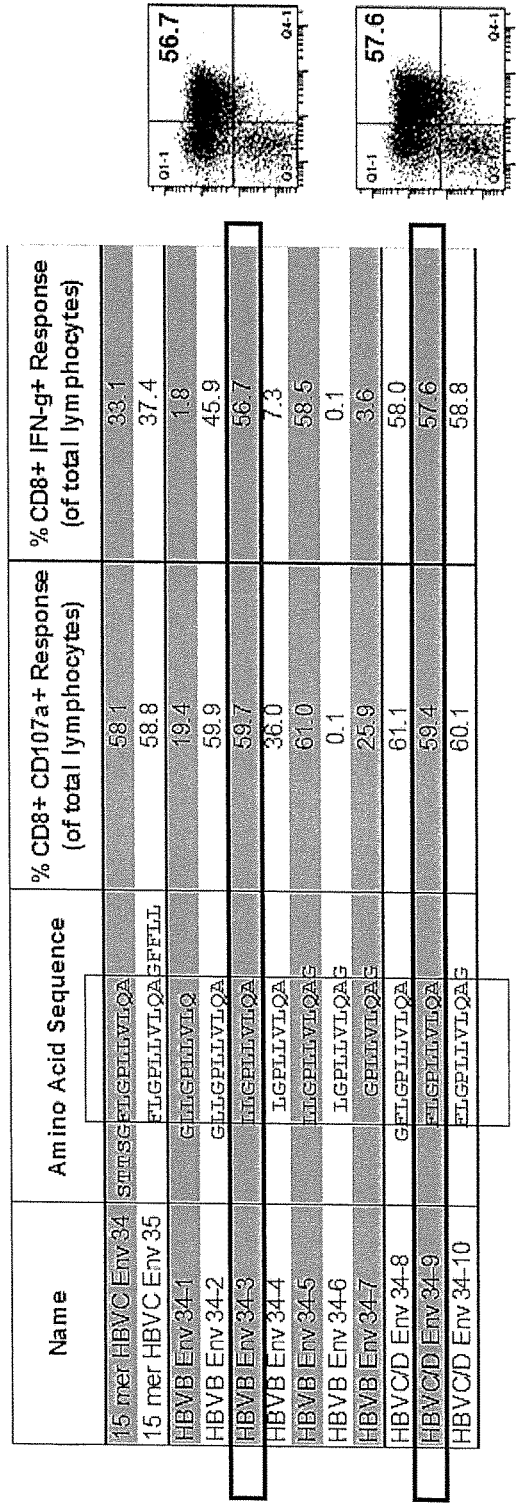
FIG. 6. Tables summarising HBV peptides and T cell responses. (A) Table showing HBV peptide sequences and positions within HBV Env. (B) Table showing the percentage of CD8+ and CD107a+, and CD8+ and IFNγ+ lymphocytes as a percentage of the total number of lymphocytes, following stimulation with the indicated peptides.

The results are shown in FIG. 6B. The frequency of CD8+ and IFNγ+ cells is highest and similar for HBV Env epitope 171-180 expressed by both HBV genotype B (LLGPLLVLQA) and HBV genotype C (FLGPLLVLQA). This shows the T cell clone's conserved specificity for both genotype B and C.

Example 3: Dose Response for HBV Genotype B and C Peptides

Epstein-Barr Virus-transformed B cells (EBVB cells) were pulsed with various concentration (1 μg/ml-1 μg/ml) of the identified HBV envelope epitopes (both genotypes B and C: F/LLGPLLVLQ) before incubation with short-term expanded T cell lines for 5 hours in the presence of BFA.

Figure 7:
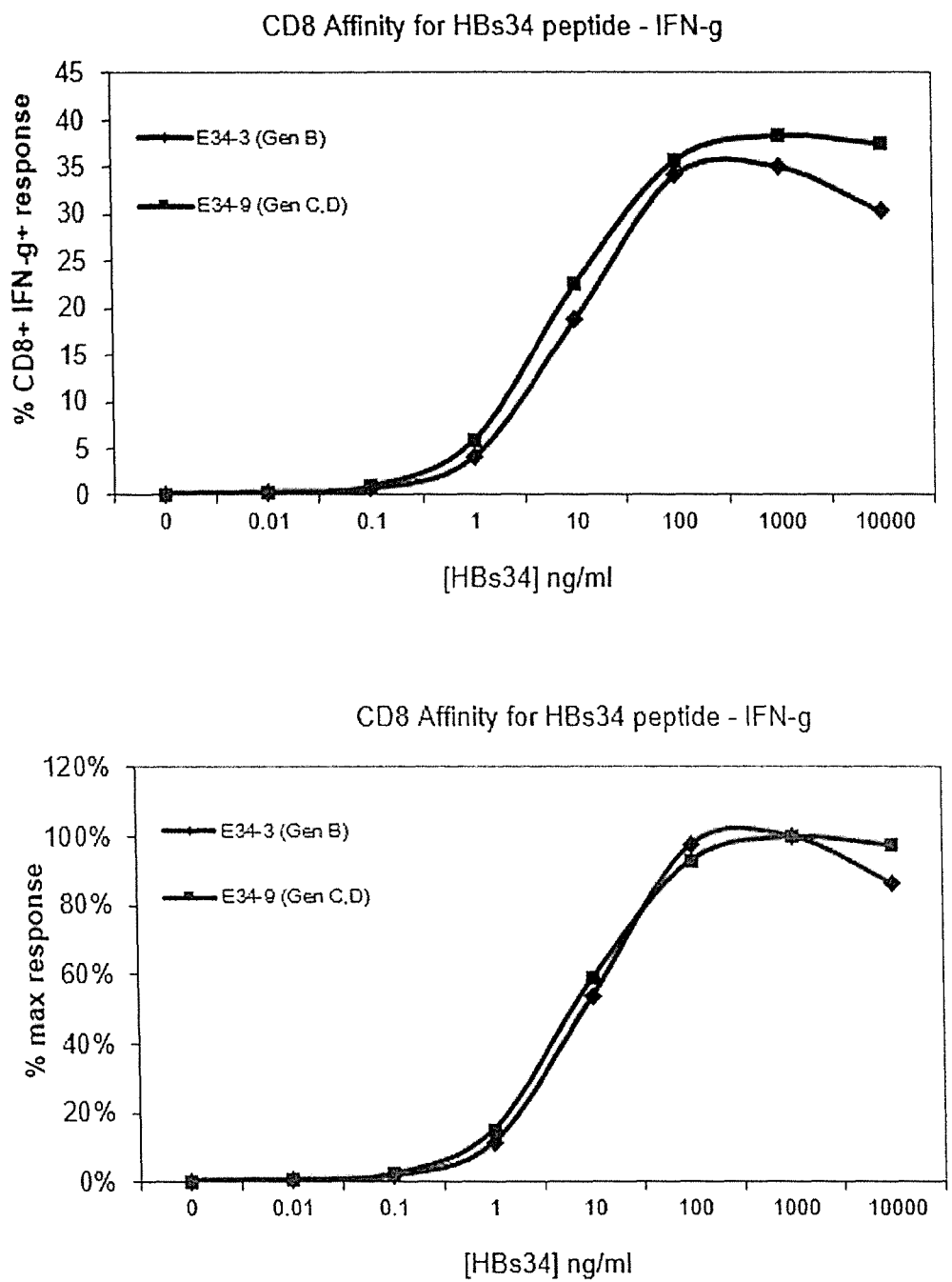
FIG. 7. Graphs showing IFNγ production by T cells stimulated with different concentrations of different HBV peptides.

The results are shown in FIG. 7. Both genotype B and C peptides elicited similar levels of IFNγ production by CD8+ T cells.

Example 4: Determining HLA Restriction

Figure 8:
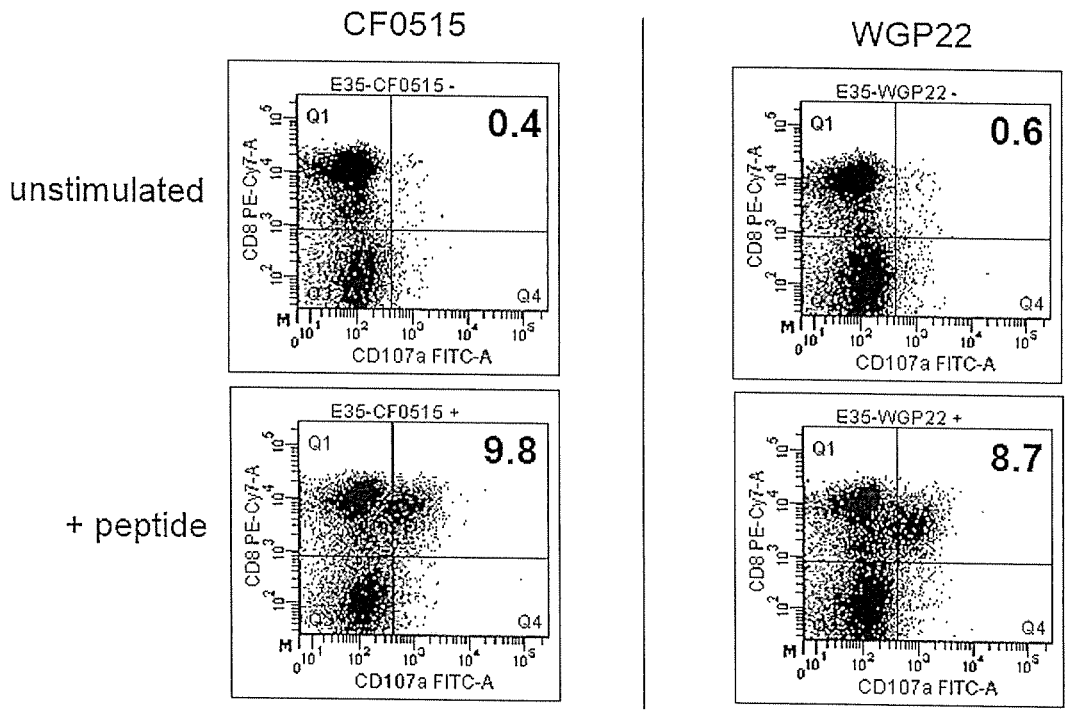
FIG. 8. Table and graphs showing analysis of donor for HLA type.

The subject's HLA type was determined to 4-digit resolution by DNA sequencing. After pulsing a panel of known HLA class I-matched EBVB cells with E35 peptides, short-term expanded T cell lines were added and cultured for 5 hours, then IFNγ and CD107a-expressing CD8+ T cells were quantified by flow cytometry. It was been determined that the expanded T cell clone was restricted by Cw0801 (see FIG. 8; CF0515 and WGP22 are immortalized EBV B cell lines).

Example 5: Clonality and TCR Cloning

Clonality of the HBV Env 171-180 specific, Cw0801 restricted T cell clone was investigated using a panel of T cell receptor Vb monoclonal antibodies. The TCR variable beta chain staining panel IO Test Beta Mark TCR V kit (Beckman Coulter) was used to determine the immunodominant Vβ on CD107a+ cells following peptide stimulation.

The T cell clone was stimulated with 1 μg/ml of peptide for 2 h in the presence of anti-CD107a-APC and washed once before staining for dominant Vb using IOTest® Beta Mark TCR V beta Repertoire Kit (Beckman Coulter, CA). This procedure stained the T cells with all known Vb chain family members. E34-specific T cells were sorted using FACS Aria III (BD Biosciences) by gating on CD107a+Vβ+ cells. The staining gave a positive staining for the particular Vb chain TRBV20.1 indicating that the clone is homogenous.

Figure 9:
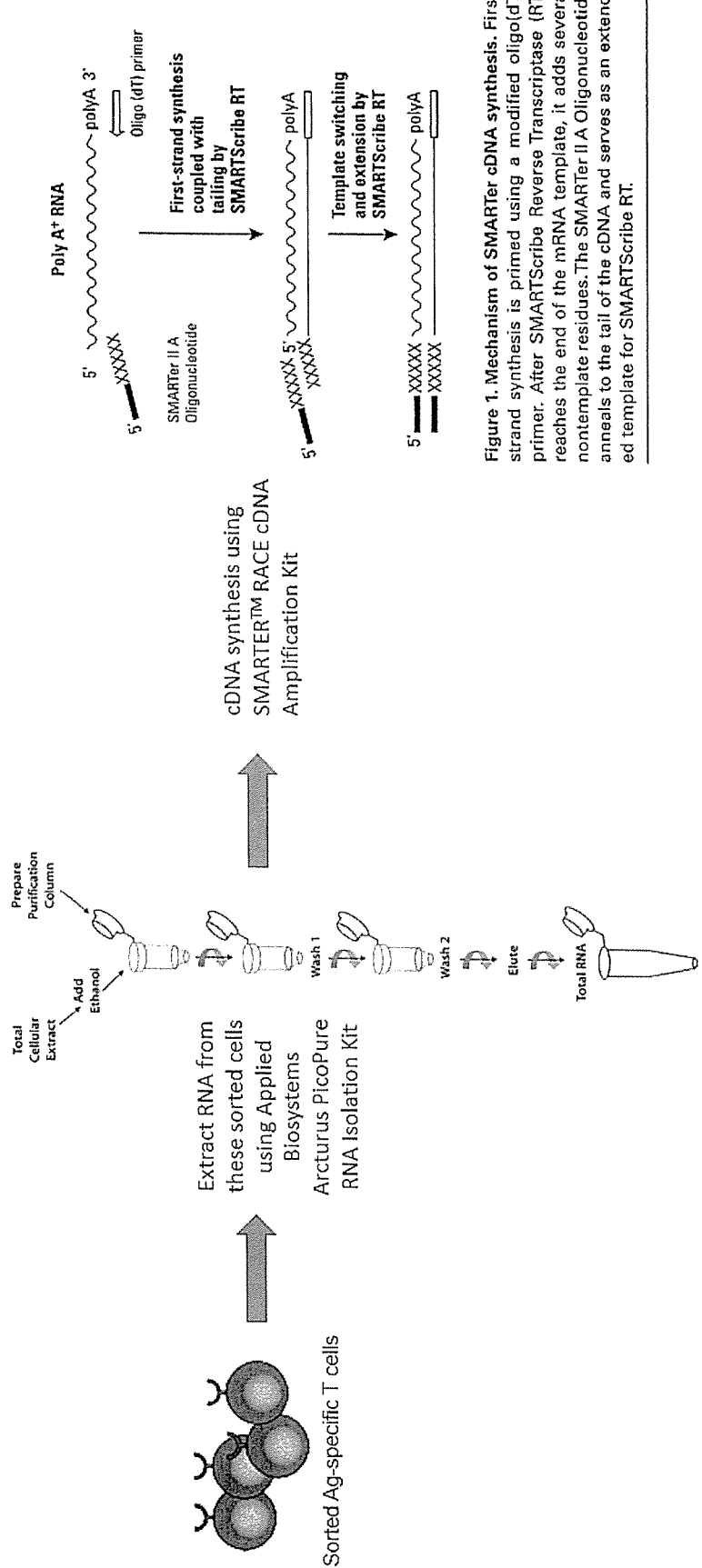
FIG. 9. Schematic representation of preparation of cDNA from T cells.
Figure 10:
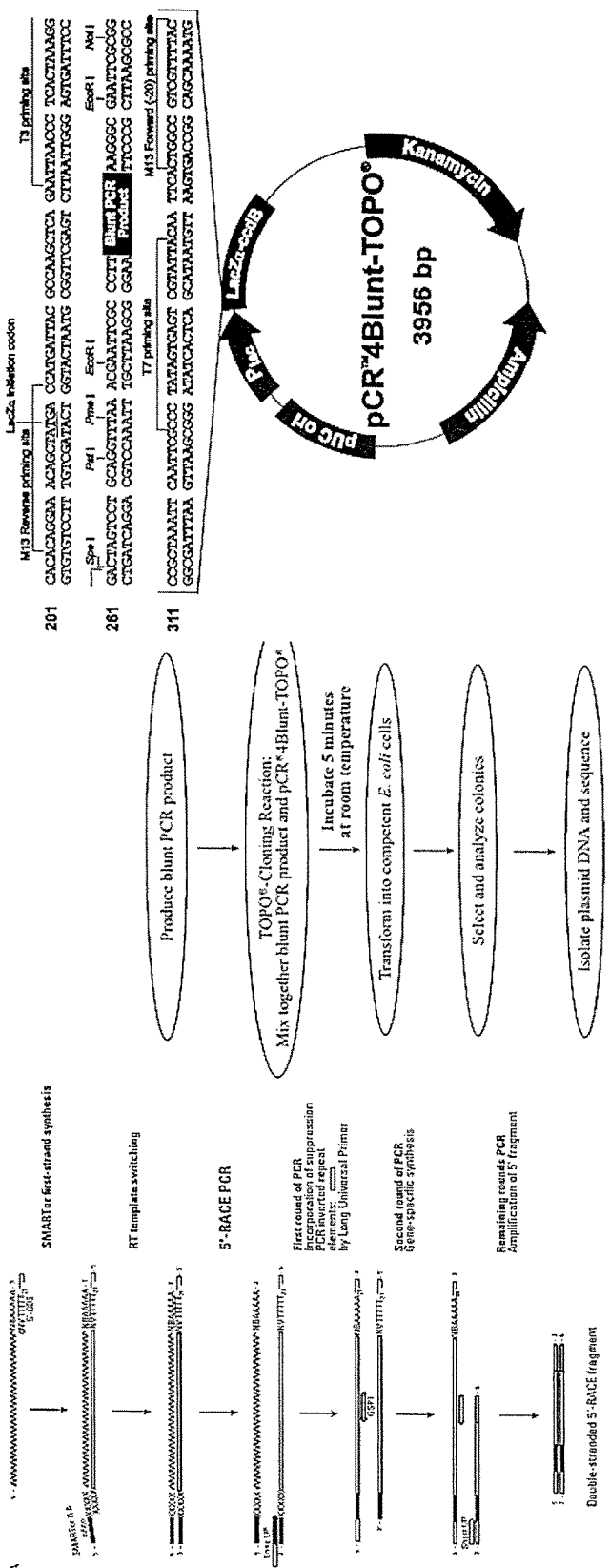
FIG. 10. Schematic representation TOPO cloning of SMARTer cDNA for bacterial transformation and sequence anaylsis.

Total RNA was isolated from the sorted T cell clones using Arcturus PicoPure RNA Isolation Kit (Applied Biosysterms) according to the manufacturer's instructions. Briefly, total cellular extract was added into the purification column and eluted with ethanol. cDNA was synthesised using SMARTER™ RACE cDNA Amplification Kit (FIG. 9). SMARTer II A oligonucleotides and oligo (dT) primer were used together with SMARTScribe Reverse Transcriptase (RT) for mRNA synthesis. SMARTScribe RT adds several non-template residues when it reaches the end of the mRNA template. The non-template tail of the mRNA template acts as an extended priming area for the second strand synthesis. After two rounds of PCR reaction, the blunt PCR products were ligated into pCR™ 4blunt-TOPO vector for bacterial transformation (FIG. 10). Sequence analysis using the immunogenetics V-quest algorithm (http://imgt.cines.fr/IMGT_vquest/share/textes/) revealed the Complementarity Determining Region (CDR) in the Va chain (CDR 1a: gacagctcctccacctac (SEQ ID NO: 7), CDR 2a: attttt-caaatatggacatg (SEQ ID NO: 8), CDR 3a: gcagagaccttgga-taactatggtcagaattttgtc (SEQ ID NO: 9)) and CDR in Vb chain (CDR 1b: gactttcaggccacaact (SEQ ID NO: 10), CDR 2b: tccaatgagggctccaaggcc (SEQ ID NO: 11), CDR 3b: agtgctgtagacagggatgaacctttccatagcaatcagccccagcat (SEQ ID NO: 12))—see FIG. 11.

A variant clone was also identified encoding a CDR1a having the amino acid sequence DISSTY (SEQ ID NO: 25).

Example 6: Functional Analysis of Retrovirally Transduced T Cells

After determination of TCR α and β chain CDR sequences, the TCR genes were cloned into MP71 retroviral vectors individually to analyse for expression and function.

Figure 12:
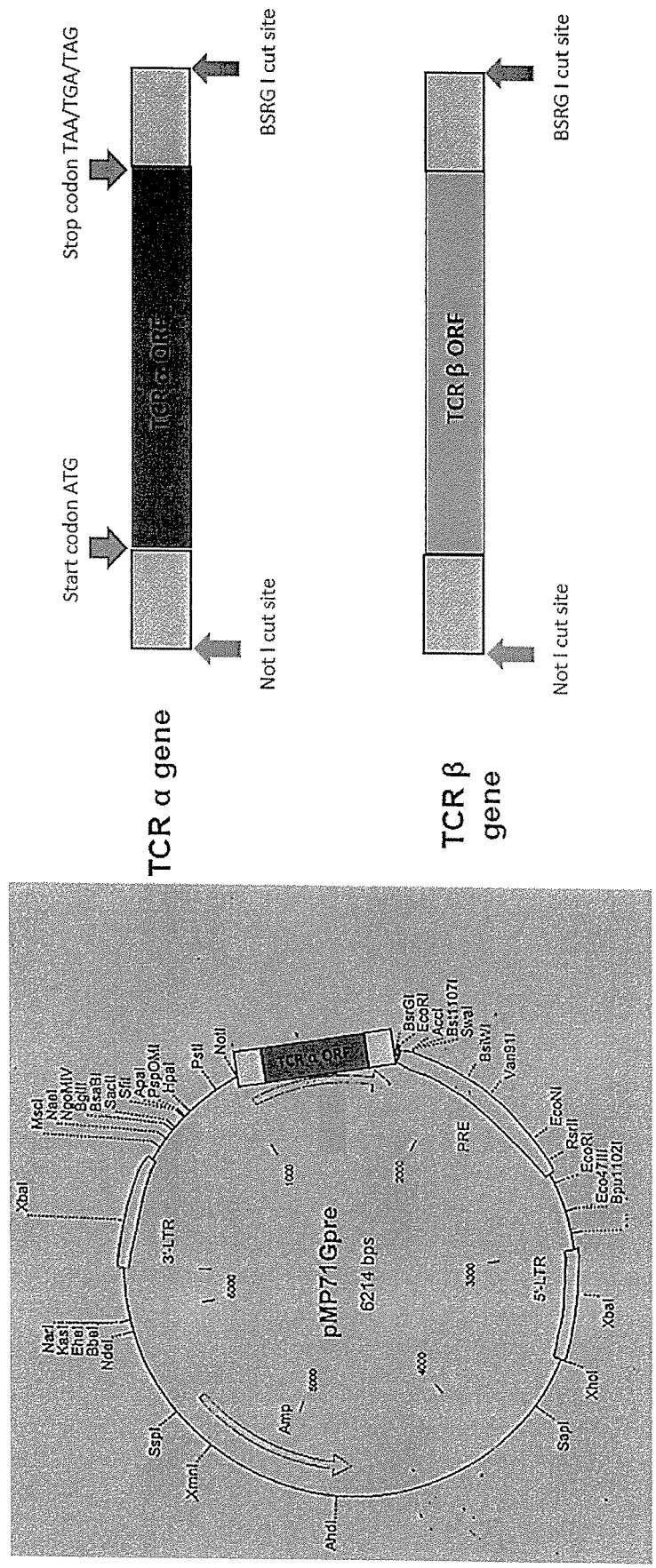
FIG. 12. Schematic representation of TCR α and TCR β chain MP71 retroviral vector constructs.
Figure 13:
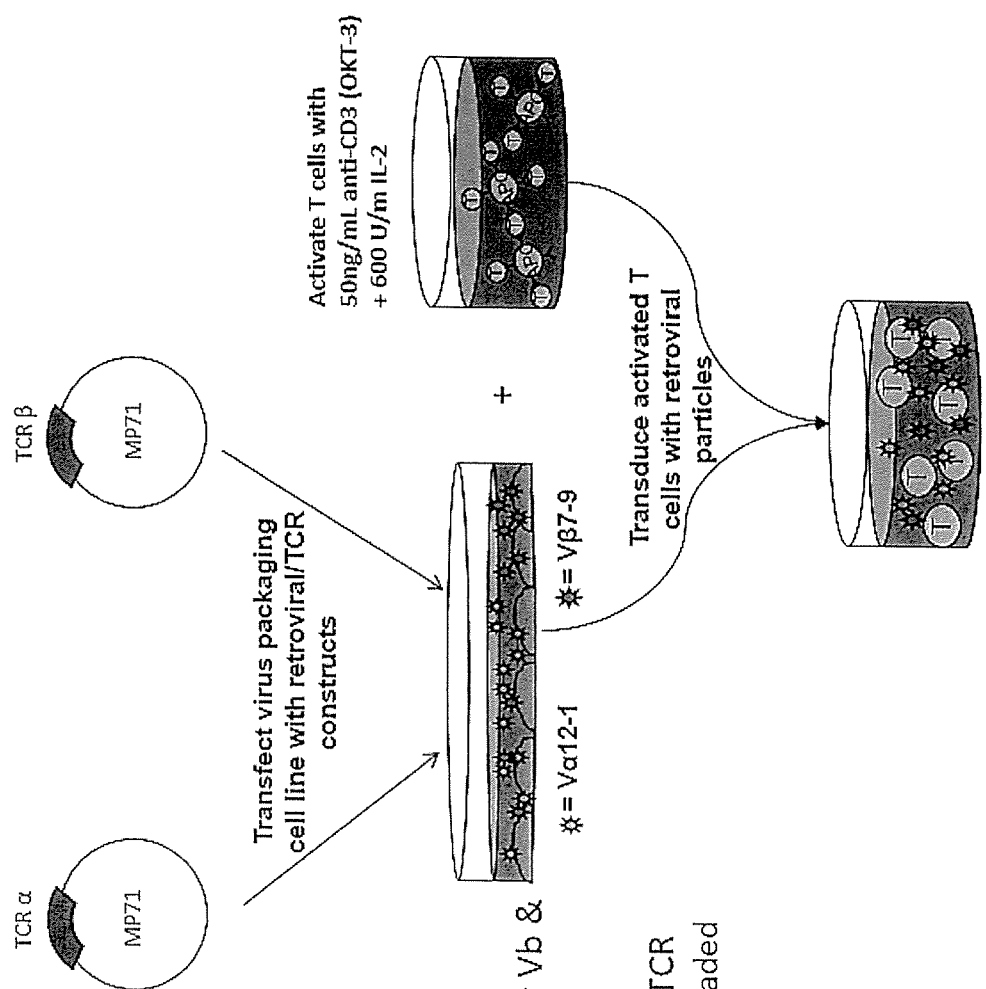
FIG. 13. Schematic representation of retrovirus preparation and transduction of T cells.

Briefly, virus packaging cell line (Clontech Laboratories, US) was seeded at $2 \times 10^6$ cells/dish together with IMDM, 10% FBS, 25 mM HEPES, Glutamax (Invitrogen) and Plasmocin (Invivogen) 1 day before transfection. On day 0, cells were transiently co-transfected with MP71 retroviral vectors using $CaCl_2$ method together with amphotropic envelope (FIGS. 12 and 13). Cells were incubated for another day in Aim-V 2% human AB serum before viral supernatants were collected and mixed with $5 \times 10^5$ activated T cells for 6 days with 50 ng/ml anti-CD3 (OKT-3, eBioscience, San Diego, Calif.) and 600 U/ml IL-2.

On day 7, the expression efficacy of the transduced TCR was determined by separately staining for Vb and pentamer, and analysis by FACs. Anti-Vbeta antibodies (Beckman Coulter) and PE labelled HLA pentamer (Prolmmune) were used. Cells were stained with with E34 Pentamer for 10 min, at room temperature, and then stained for Vb and CD8 for 30 min, on ice before being acquired by FACs.

Figure 14:
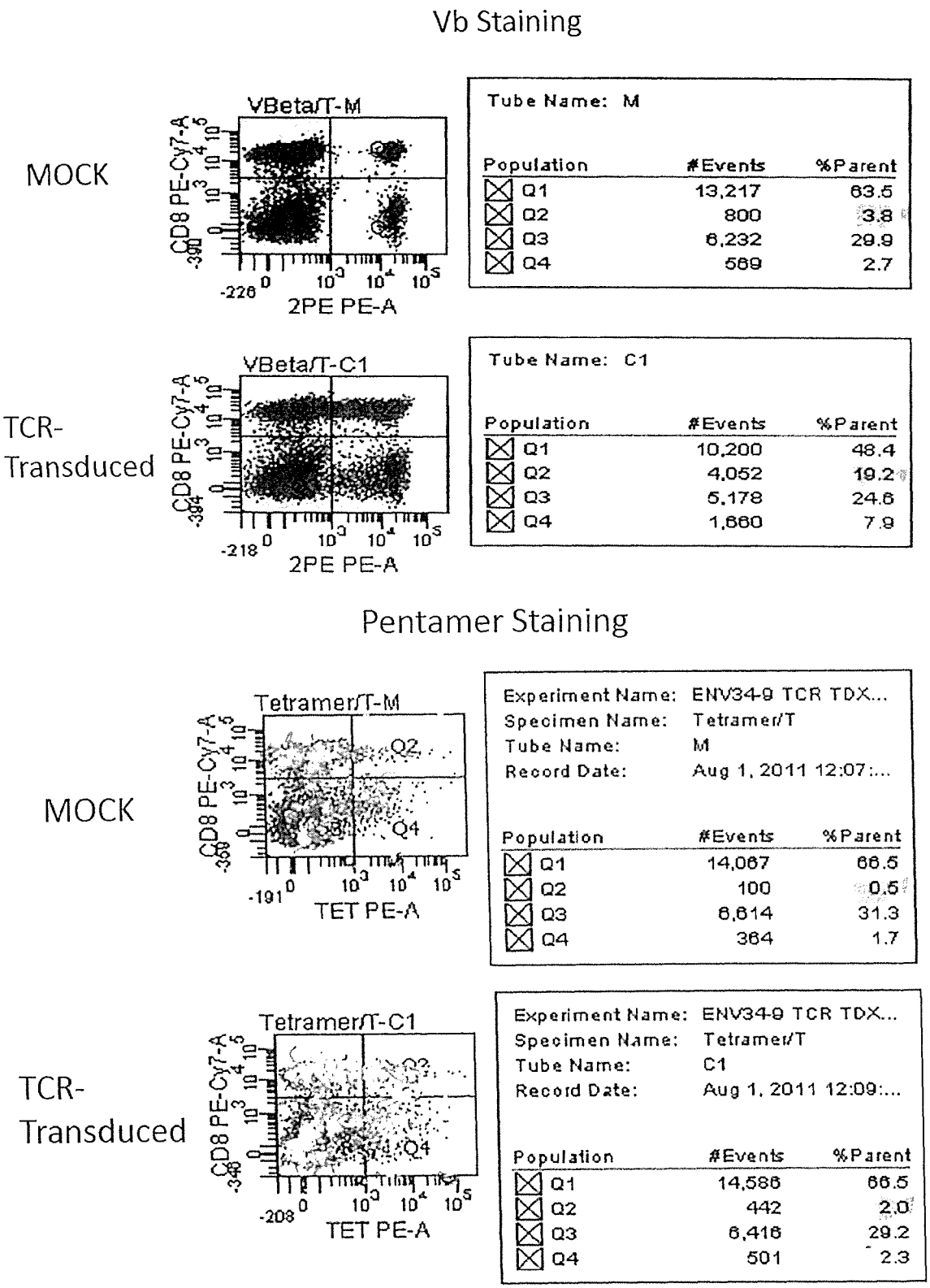
FIG. 14. Graphs showing Vb expression and E34 pentamer binding by CD8+ T cells transduced with TCR α and TCR β constructs as compared to non-transduced controls.

The transduced T cells showed increased Vb expression and pentamer binding as compared to mock transduced cells (FIG. 14).

On day 10, activated EBVB cells were used to confirm the functionality of the transduced T cells by degranulation assay.

Briefly, EBVB cell line CF0515 (which encodes the HLA-C allele HLA-Cw*0801) was pulsed with 10 μg/mL of peptide for 1 h at room temperature. Peptide-pulsed cells were then co-cultured with TCR transduced cells or mock transduced cells in the presence of CD107a and BFA, and incubated overnight at 37° C.

HBs171-180 TCR transduced T cells and mock transduced T cells were labelled with CD8 and CD107a antibody, permeabilised by cytofix/cytoperm and stained for anti-IFNγ PE, washed, and analysed by flow cytometry.

Figure 15:
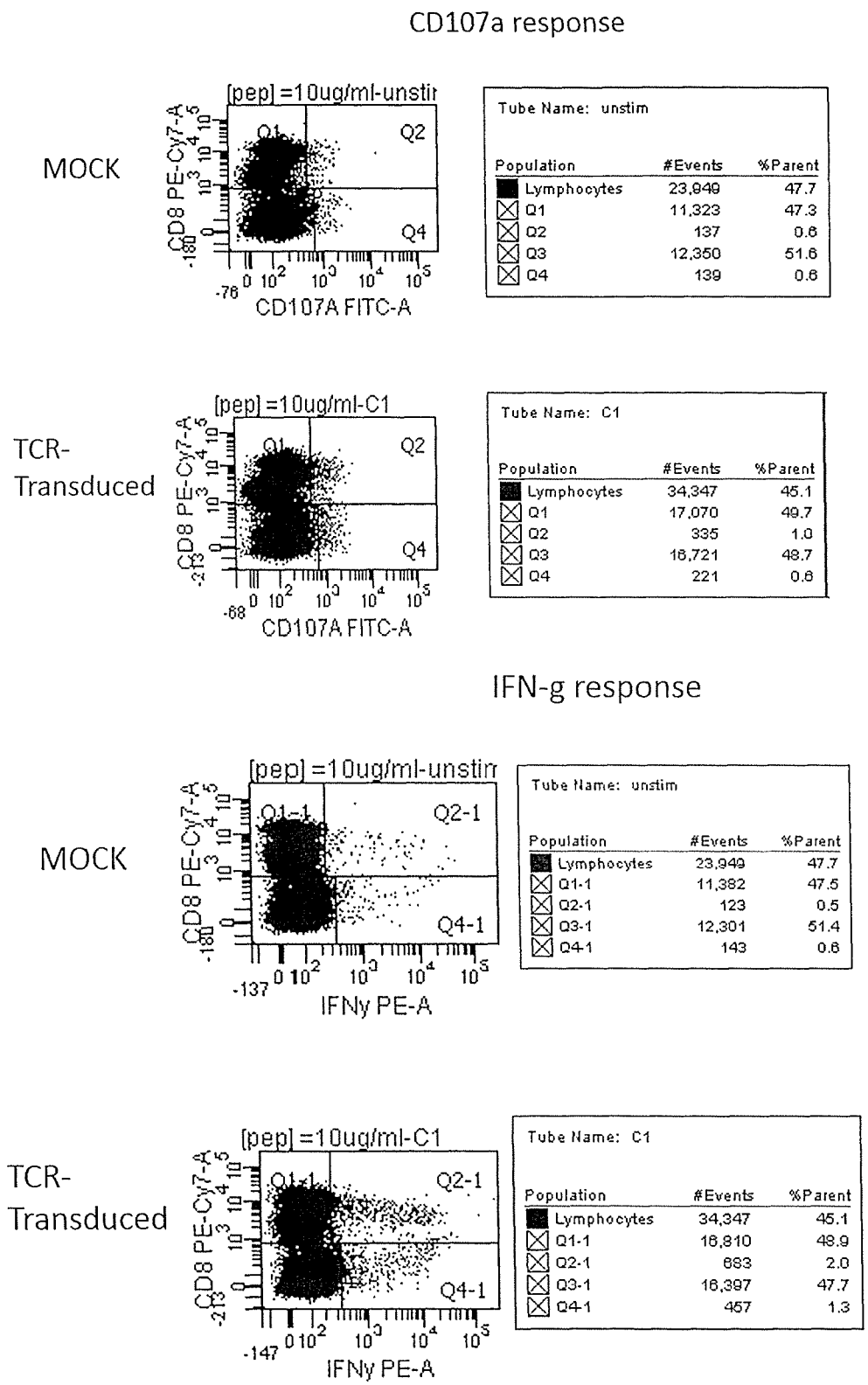
FIG. 15. Graphs showing expression of CD107a and IFNγ by CD8+ T cells transduced with TCR α and TCR β constructs as compared to non-transduced controls, following incubation with peptide-pulsed EBVB cells.

The results are shown in FIG. 15. A clear increase in the frequency of CD8+ CD107a+ T cell population and IFNγ secreting CD8 T cells was observed.

Example 7: Codon Optimisation and Vector Construction

The TCR genes were further optimised and constructed into a single cassette. Two amino acids changes were incorporated into the TCR α chain constant region and one in the β chain constant region to increase pairing and expression.

Gene cassettes consisting of Vα-P2A-Vβ and Vβ-P2A-Vα orientations were cloned into MP71 to produce two different P2A-linked single cassette, codon optimized, cysteine-modified gene constructs (Genscript), with the TCR α and β chains in different orientations (see FIG. 16).

Colonies were screened, and the constructs were transduced into primary human T cells to investigate expression and functionality.

Expression efficiency was tested by Vb staining and pentamer staining after transduction, and the results are shown in FIG. 17. Anti-Vbeta antibodies and PE labeled HLA pentamers were used to monitor expression of transduced TCR as above.

When the coding sequence for the β chain was positioned in the expression cassette 5' to the coding sequence for the α chain, two-fold increase in Vb staining was seen while a remarkable 7-fold increase in pentamer staining, indicating a correctly paired TCR, was observed.

Figure 18:
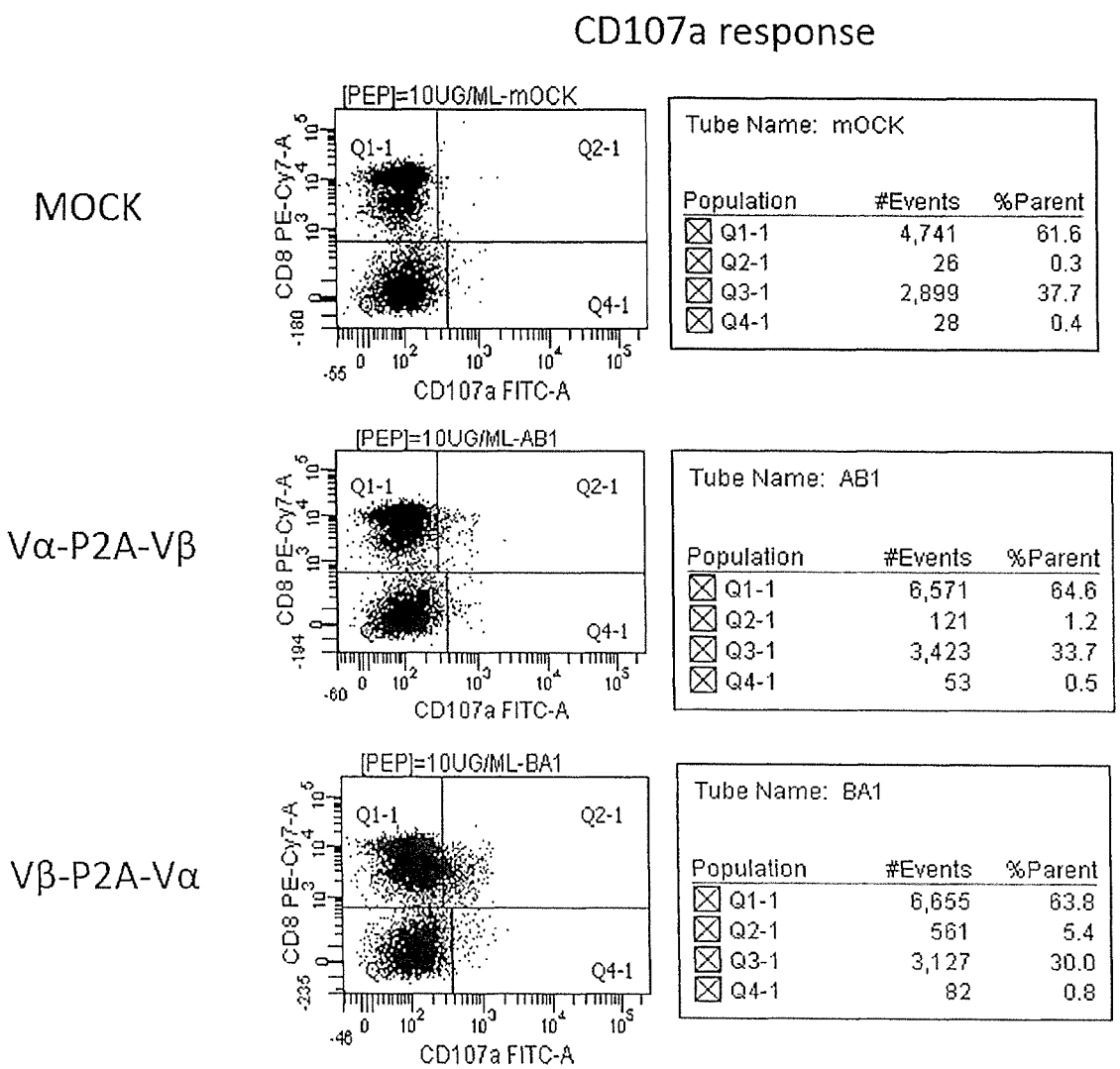
FIG. 18. Graphs showing expression of CD107a and IFNγ by CD8+ T cells transduced with Vα-P2A-Vβ and Vβ-P2A-Vα constructs, following incubation with peptide-pulsed EBVB cells.
Figure 18:
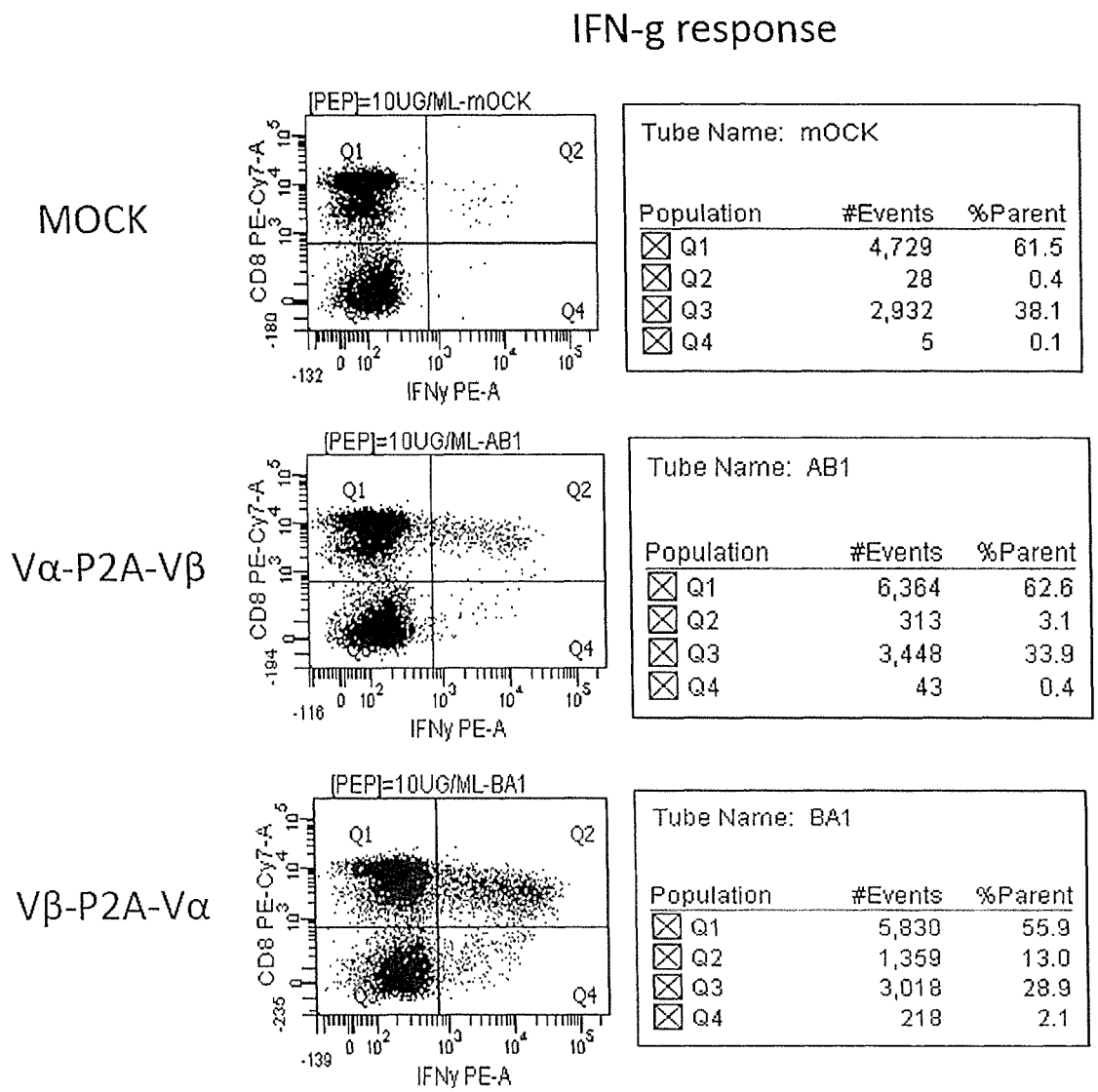

The frequency virus-specific CD8 T cells was determined by analysis of degranulation and IFNγ production, and the results are shown in FIG. 18. Increased expression of the functional TCR translated into more than 4-fold increase in functionality.

The invention claimed is:

1. A T Cell Receptor (TCR), or a fragment thereof, optionally isolated, comprising:

a TCR α-chain variable region comprising a CDR3a having the amino acid sequence:

CDR3a:
(SEQ ID NO: 3)
AETLDNYGQNFV, or a variant thereof in which one or two amino acids are replaced with another amino acid;
and;
a TCR β-chain variable region comprising a CDR3b having the amino acid sequence:

CDR3b:
(SEQ ID NO: 6)
SAVDRDEPFHSNQPQH or a variant thereof in which one or two amino acids are replaced with another amino acid.

2. A T Cell Receptor (TCR), or a fragment thereof, optionally isolated, comprising:

a TCR α-chain variable region comprising CDRs having the amino acid sequences i) to):

i) CDR1 a:
(SEQ ID NO: 1)
DXSSTY;

ii) CDR2a:
(SEQ ID NO: 2)
IFSNMDM;

iii) CDR3a:
(SEQ ID NO: 3)
AETLDNYGQNFV;

or a variant thereof in which one or two amino acids in one or more of the sequences i) to iii) are replaced with another amino acid; where X=S or I.

3. A T Cell Receptor (TCR), or a fragment thereof, optionally isolated, comprising: a TCR β-chain variable region comprising CDRs having the amino acid sequences iv) to vi):

```
iv) CDR1b:
                        (SEQ ID NO: 4)
DFQATT;

v) CDR2b:
                        (SEQ ID NO: 5)
SNEGSKA;

vi) CDR3b:
                        (SEQ ID NO: 6)
SAVDRDEPFHSNQPQH;
``` or a variant thereof in which one or two amino acids in one or more of the sequences iv) to are replaced with another amino acid.

4. The TCR or a fragment according to claim 1, comprising:

a TCR α-chain variable region comprising CDRs having the amino acid sequences i) to iii):

```
i) CDR1 a:
                        (SEQ ID NO: 1)
DXSSTY;

ii) CDR2a:
                        (SEQ ID NO: 2)
IFSNMDM;

iii) CDR3a:
                        (SEQ ID NO: 3)
AETLDNYGQNFV;
``` and;

a TCR β-chain variable region comprising CDRs having the amino acid sequences iv) to vi):

```
iv) CDR1 b:
                        (SEQ ID NO: 4)
DFQATT;

v) CDR2b:
                        (SEQ ID NO: 5)
SNEGSKA;

vi) CDR3b:
                        (SEQ ID NO: 6)
SAVDRDEPFHSNQPQH;
``` or a variant thereof in which one or two amino acids in one or more of the sequences i) to vi) are replaced with another amino acid;
where X=S or I.

5. An isolated nucleic acid encoding a TCR or fragment according to claim 1.

6. The isolated nucleic acid according to claim 5, wherein the nucleic acid comprises:
(a) a nucleic acid sequence encoding a TCR α-chain comprising a variable region and a constant region;
(b) a nucleic acid sequence encoding a TCR β-chain comprising a variable region and a constant region; and
(c) a nucleic acid sequence encoding a cleavable linker;
wherein sequence (c) is located in the isolated nucleic acid between sequences (a) and (b), and
wherein sequences (a), (b) and (c) are in the same reading frame.

7. The isolated nucleic acid according to claim 6, wherein sequences (a), (b) and (c) are provided with the 5' to 3' orientation: 5'-(b)-(c)-(a)-3'.

8. The isolated nucleic acid according to claim 6, wherein the cleavable linker is a Picornavirus 2A (P2A) linker.

9. The isolated nucleic acid according to claim 6, wherein the constant region of the TCR α-chain and/or the constant region of the TCR β-chain additionally encode at least one non-native cysteine residue for forming a disulphide bond between the TCR α-chain and TCR β-chain.

10. A vector comprising the isolated nucleic acid according to claim 5, wherein the vector is selected from a group consists of plasmids, binary vectors, DNA vectors, mRNA vectors, retrovial vectors, lentiviral vectors, transposon-based vectors, and artificial chromosomes.

11. An isolated polypeptide encoded by the isolated nucleic acid according to claim 5.

12. A cell, optionally isolated, comprising the TCR or fragment according to claim 1.

13. The cell according to claim 12, wherein the cell displays one or more of the following properties:
a) expression of IFNγ;
h) cytotoxicity to a cell infected with HBV or comprising or expressing an HBV Env peptide or polypeptide;
c) proliferation, increased IFN-' expression, increased IL-2 expression, increased TNFα expression, increased perforin expression, increased granzyme expression and/or increased FAS ligand (FASL) expression in response to contact with a cell infected with HBV or comprising or expressing an HBV Env peptide or polypeptides.

14. An in vitro method of producing a Hepatitis B Virus (HBV) reactive T cell, comprising introducing into a cell the isolated nucleic acid according to claim 5.

15. The method of claim 14, wherein the method additionally comprises culturing the cell under conditions suitable for expression of the isolated nucleic acid or vector by the cell.

16. A cell, optionally isolated, wherein the cell is obtained or obtainable by the method of claim 14.

17. A complex, optionally an in vitro complex, comprising the TCR or fragment according to claim 1, and a Hepatitis B Virus (HBV) Env peptide or polypeptide, optionally further comprising an MHC class I molecule comprising an MHC class I α-chain encoded by an HLA-Cw*08 allele.

18. A pharmaceutical composition comprising a TCR or fragment according to claim 1, and a pharmaceutically acceptable carrier, adjuvant, excipient, or diluent.

19. A method of treating or preventing a disease or disorder in a subject, comprising:
(a) isolating at least one T cell from a subject;
(b) introducing into the at least one T cell the isolated nucleic acid according to claim 5, thereby modifying the at least one T cell; and
(c) administering the modified at least one T cell to the subject.

20. An in vitro method for preparing a modified T cell, the method comprising introducing into a T cell the TCR or fragment according to claim 8.

21. A kit of parts comprising a predetermined quantity of the TCR or fragment according to claim 1.

* * * * *

SEQUENCE LISTING

```
<160> NUMBER OF SEQ ID NOS: 39

<210> SEQ ID NO 1
<211> LENGTH: 6
<212> TYPE: PRT
<213> ORGANISM: Artificial Sequence
<220> FEATURE:
<223> OTHER INFORMATION: CDR 1a
<220> FEATURE:
<221> NAME/KEY: VARIANT
<222> LOCATION: (2)..(2)
<223> OTHER INFORMATION: Xaa is either Ser or Ile

<400> SEQUENCE: 1

Asp Xaa Ser Ser Thr Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: CDR2a

<400> SEQUENCE: 2

Ile Phe Ser Asn Met Asp Met
1               5

<210> SEQ ID NO 3
<211> LENGTH: 12
<212> TYPE: PRT
<213> ORGANISM: Artificial Sequence
<220> FEATURE:
<223> OTHER INFORMATION: CDR3a

<400> SEQUENCE: 3

Ala Glu Thr Leu Asp Asn Tyr Gly Gln Asn Phe Val
1               5                   10

<210> SEQ ID NO 4
<211> LENGTH: 6
<212> TYPE: PRT
<213> ORGANISM: Artificial Sequence
<220> FEATURE:
<223> OTHER INFORMATION: CDR1b

<400> SEQUENCE: 4

Asp Phe Gln Ala Thr Thr
1               5

<210> SEQ ID NO 5
<211> LENGTH: 7
<212> TYPE: PRT
<213> ORGANISM: Artificial Sequence
<220> FEATURE:
<223> OTHER INFORMATION: CDR2b
```

```
<400> SEQUENCE: 5

Ser Asn Glu Gly Ser Lys Ala
1               5

<210> SEQ ID NO 6
<211> LENGTH: 16
<212> TYPE: PRT
<213> ORGANISM: Artificial Sequence
<220> FEATURE:
<223> OTHER INFORMATION: CDR3b

<400> SEQUENCE: 6

Ser Ala Val Asp Arg Asp Glu Pro Phe His Ser Asn Gln Pro Gln His
1               5                   10                  15

<210> SEQ ID NO 7
<211> LENGTH: 18
<212> TYPE: DNA
<213> ORGANISM: Artificial Sequence
<220> FEATURE:
<223> OTHER INFORMATION: CDR1a

<400> SEQUENCE: 7
gacagctcct ccacctac                                                 18

<210> SEQ ID NO 8
<211> LENGTH: 21
<212> TYPE: DNA
<213> ORGANISM: Artificial Sequence
<220> FEATURE:
<223> OTHER INFORMATION: CDR2a

<400> SEQUENCE: 8
attttttcaa atatggacat g                                             21

<210> SEQ ID NO 9
<211> LENGTH: 36
<212> TYPE: DNA
<213> ORGANISM: Artificial Sequence
<220> FEATURE:
<223> OTHER INFORMATION: CDR3a

<400> SEQUENCE: 9
gcagagacct tggataacta tggtcagaat tttgtc                             36

<210> SEQ ID NO 10
<211> LENGTH: 18
<212> TYPE: DNA
<213> ORGANISM: Artificial Sequence
<220> FEATURE:
<223> OTHER INFORMATION: CDR1b

<400> SEQUENCE: 10
gactttcagg ccacaact                                                 18

<210> SEQ ID NO 11
<211> LENGTH: 21
<212> TYPE: DNA
<213> ORGANISM: Artificial Sequence
<220> FEATURE:
<223> OTHER INFORMATION: CDR2b

<400> SEQUENCE: 11
tccaatgagg gctccaaggc c                                             21
```

<210> SEQ ID NO 12
<211> LENGTH: 48
<212> TYPE: DNA
<213> ORGANISM: Artificial Sequence
<220> FEATURE:
<223> OTHER INFORMATION: CDR3b

<400> SEQUENCE: 12
agtgctgtag acagggatga acctttccat agcaatcagc cccagcat        48

<210> SEQ ID NO 13
<211> LENGTH: 18
<212> TYPE: DNA
<213> ORGANISM: Artificial Sequence
<220> FEATURE:
<223> OTHER INFORMATION: CDR1a

<400> SEQUENCE: 13
gactcctcta gtacctac        18

<210> SEQ ID NO 14
<211> LENGTH: 21
<212> TYPE: DNA
<213> ORGANISM: Artificial Sequence
<220> FEATURE:
<223> OTHER INFORMATION: CDR2a

<400> SEQUENCE: 14
atcttttcca acatggacat g        21

<210> SEQ ID NO 15
<211> LENGTH: 36
<212> TYPE: DNA
<213> ORGANISM: Artificial Sequence
<220> FEATURE:
<223> OTHER INFORMATION: CDR3a

<400> SEQUENCE: 15
gccgagaccc tggacaacta cggccagaat ttcgtg        36

<210> SEQ ID NO 16
<211> LENGTH: 18
<212> TYPE: DNA
<213> ORGANISM: Artificial Sequence
<220> FEATURE:
<223> OTHER INFORMATION: CDR1b

<400> SEQUENCE: 16
gacttccagg ccaccaca        18

<210> SEQ ID NO 17
<211> LENGTH: 21
<212> TYPE: DNA
<213> ORGANISM: Artificial Sequence
<220> FEATURE:
<223> OTHER INFORMATION: CDR2b

<400> SEQUENCE: 17
agcaacgaag gatccaaagc c        21

<210> SEQ ID NO 18
<211> LENGTH: 48
<212> TYPE: DNA
<213> ORGANISM: Artificial Sequence
<220> FEATURE:
<223> OTHER INFORMATION: CDR3b

<400> SEQUENCE: 18
tcagcagtgg accgagatga acctttccac agcaaccagc cacagcat            48

<210> SEQ ID NO 19
<211> LENGTH: 10
<212> TYPE: PRT
<213> ORGANISM: Artificial Sequence
<220> FEATURE:
<223> OTHER INFORMATION: HBV Gen C

<400> SEQUENCE: 19

Phe Leu Gly Pro Leu Leu Val Leu Gln Ala
1               5                   10

<210> SEQ ID NO 20
<211> LENGTH: 10
<212> TYPE: PRT
<213> ORGANISM: Artificial Sequence
<220> FEATURE:
<223> OTHER INFORMATION: HBV Gen B

<400> SEQUENCE: 20

Leu Leu Gly Pro Leu Leu Val Leu Gln Ala
1               5                   10

<210> SEQ ID NO 21
<211> LENGTH: 15
<212> TYPE: PRT
<213> ORGANISM: Artificial Sequence
<220> FEATURE:
<223> OTHER INFORMATION: HBV Gen C

<400> SEQUENCE: 21

Ser Thr Thr Ser Gly Phe Leu Gly Pro Leu Leu Val Leu Gln Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: HBV Gen B

<400> SEQUENCE: 22

Ser Thr Thr Ser Gly Leu Leu Gly Pro Leu Leu Val Leu Gln Ala
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: HBV Gen B and C

<400> SEQUENCE: 23

Val Leu Gln Ala Gly Phe Phe Leu Leu Thr Arg Ile Leu Thr
1               5                   10

<210> SEQ ID NO 24
<211> LENGTH: 6
<212> TYPE: PRT
<213> ORGANISM: Artificial Sequence
<220> FEATURE:
<223> OTHER INFORMATION: CDR1a

<400> SEQUENCE: 24

```
Asp Ser Ser Ser Thr Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: CDR1a

<400> SEQUENCE: 25

Asp Ile Ser Ser Thr Tyr
1               5

<210> SEQ ID NO 26
<211> LENGTH: 11
<212> TYPE: PRT
<213> ORGANISM: Artificial Sequence
<220> FEATURE:
<223> OTHER INFORMATION: HBVC/D Env 34-10

<400> SEQUENCE: 26

Phe Leu Gly Pro Leu Leu Val Leu Gln Ala Gly
1               5                   10

<210> SEQ ID NO 27
<211> LENGTH: 14
<212> TYPE: PRT
<213> ORGANISM: Artificial Sequence
<220> FEATURE:
<223> OTHER INFORMATION: HBV Gen C

<400> SEQUENCE: 27

Ser Thr Thr Ser Gly Phe Leu Gly Pro Leu Leu Val Leu Gln
1               5                   10

<210> SEQ ID NO 28
<211> LENGTH: 15
<212> TYPE: PRT
<213> ORGANISM: Artificial Sequence
<220> FEATURE:
<223> OTHER INFORMATION: HBV Gen C

<400> SEQUENCE: 28

Phe Leu Gly Pro Leu Leu Val Leu Gln Ala Gly Phe Phe Leu Leu
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: HBV Gen B

<400> SEQUENCE: 29

Leu Leu Gly Pro Leu Leu Val Leu Gln Ala Gly Phe Phe Leu Leu
1               5                   10                  15

<210> SEQ ID NO 30
<211> LENGTH: 25
<212> TYPE: PRT
<213> ORGANISM: Artificial Sequence
<220> FEATURE:
<223> OTHER INFORMATION: HBV Gen C

<400> SEQUENCE: 30

Ser Thr Thr Ser Gly Phe Leu Gly Pro Leu Leu Val Leu Gln Ala Gly
1               5                   10                  15
```

```
1               5                   10                  15
Phe Phe Leu Leu Thr Arg Ile Leu Thr
            20                  25

<210> SEQ ID NO 31
<211> LENGTH: 25
<212> TYPE: PRT
<213> ORGANISM: Artificial Sequence
<220> FEATURE:
<223> OTHER INFORMATION: HBV Gen B

<400> SEQUENCE: 31

Ser Thr Thr Ser Gly Leu Leu Gly Pro Leu Leu Val Leu Gln Ala Gly
1               5                   10                  15

Phe Phe Leu Leu Thr Arg Ile Leu Thr
            20                  25

<210> SEQ ID NO 32
<211> LENGTH: 10
<212> TYPE: PRT
<213> ORGANISM: Artificial Sequence
<220> FEATURE:
<223> OTHER INFORMATION: HBVB Env 34-1

<400> SEQUENCE: 32

Gly Leu Leu Gly Pro Leu Leu Val Leu Gln
1               5                   10

<210> SEQ ID NO 33
<211> LENGTH: 11
<212> TYPE: PRT
<213> ORGANISM: Artificial Sequence
<220> FEATURE:
<223> OTHER INFORMATION: HBVB Env 34-2

<400> SEQUENCE: 33

Gly Leu Leu Gly Pro Leu Leu Val Leu Gln Ala
1               5                   10

<210> SEQ ID NO 34
<211> LENGTH: 9
<212> TYPE: PRT
<213> ORGANISM: Artificial Sequence
<220> FEATURE:
<223> OTHER INFORMATION: HBVB 34-4

<400> SEQUENCE: 34

Leu Gly Pro Leu Leu Val Leu Gln Ala
1               5

<210> SEQ ID NO 35
<211> LENGTH: 11
<212> TYPE: PRT
<213> ORGANISM: Artificial Sequence
<220> FEATURE:
<223> OTHER INFORMATION: HBVB Env 34-5

<400> SEQUENCE: 35

Leu Leu Gly Pro Leu Leu Val Leu Gln Ala Gly
1               5                   10

<210> SEQ ID NO 36
<211> LENGTH: 10
<212> TYPE: PRT
<213> ORGANISM: Artificial Sequence
<220> FEATURE:
```

```
<223> OTHER INFORMATION: HBVB Env 34-6

<400> SEQUENCE: 36

Leu Gly Pro Leu Leu Val Leu Gln Ala Gly
1               5                   10

<210> SEQ ID NO 37
<211> LENGTH: 9
<212> TYPE: PRT
<213> ORGANISM: Artificial Sequence
<220> FEATURE:
<223> OTHER INFORMATION: HBVB Env 34-7

<400> SEQUENCE: 37

Gly Pro Leu Leu Val Leu Gln Ala Gly
1               5

<210> SEQ ID NO 38
<211> LENGTH: 11
<212> TYPE: PRT
<213> ORGANISM: Artificial Sequence
<220> FEATURE:
<223> OTHER INFORMATION: HBVC/D Env 34-8

<400> SEQUENCE: 38

Gly Phe Leu Gly Pro Leu Leu Val Leu Gln Ala
1               5                   10

<210> SEQ ID NO 39
<211> LENGTH: 170
<212> TYPE: DNA
<213> ORGANISM: Artificial Sequence
<220> FEATURE:
<223> OTHER INFORMATION: pCR 4Blunt-TOPO

<400> SEQUENCE: 39
cacacaggaa acagctatga ccatgattac gccaagctca gaattaaccc tcactaaagg      60
gactagtcct gcaggtttaa acgaattcgc ccttaagggc gaattcgcgg ccgctaaatt    120
caattcgccc tatagtgagt cgtattacaa ttcactggcc gtcgttttac               170
```